United States Patent [19]
Friedman et al.

[11] Patent Number: 4,543,957
[45] Date of Patent: Oct. 1, 1985

[54] HUMAN RESPONSE APPARATUS AND METHOD

[75] Inventors: Ernest H. Friedman, 1831 Forest Hills Blvd., East Cleveland, Ohio 44112; Gary G. Sanders, Lakewood, Ohio; Steven L. Hunter, Livermore, Calif.

[73] Assignee: Ernest H. Friedman, East Cleveland, Ohio

[21] Appl. No.: 503,821

[22] Filed: Jun. 13, 1983

[51] Int. Cl.$^4$ .............................................. A61B 5/00
[52] U.S. Cl. ................................... 128/630; 128/695; 128/773; 364/413
[58] Field of Search ............... 128/630, 695, 773, 777, 128/745; 364/413

[56] References Cited
U.S. PATENT DOCUMENTS

| | | |
|---|---|---|
| 3,818,609 | 6/1974 | Woolman . |
| 4,156,423 | 5/1979 | Friedman et al. . |
| 4,278,096 | 7/1981 | Friedman et al. ................... 128/695 |
| 4,278,096 | 7/1981 | Friedman et al. . |
| 4,351,983 | 9/1982 | Crouse et al. . |

FOREIGN PATENT DOCUMENTS 0959755  9/1982  U.S.S.R. .............................. 128/745

OTHER PUBLICATIONS

Emrich, H. M. et al., "Evaluation of Speech and Language in Neuropsychiatric Disorders", Arch. Psychiat. Nervenki, 225, pp. 209–221, (1978).
Circulation, 66:83, 1982, "Feasibility of Altering Type A Behavior Pattern After Myocardial Infarction".
Science, 218:31, 1982.
The Sciences, Feb. 1982, "The Divided Self".
Clinical Psychiatry News, Jul. 1982, "Hemisphere Involved May be Specific for Type of Depression".
Heart & Lung: The Journal of Critical Care 11:26, 1982, "Stress and Intensive-Care Nursing: A Ten-Year Reappraisal".
"Method and Monitor for Voice Fluency", U.S. Pat. No. 4,377,158, Issued Mar. 22, 1983.
Heart & Lung, 1:753, 1972, "Stress and Intensive-Care Nursing".
Psychiatric News–Aug. 6, 1982, "Brain Hemispheres Function as Unit in Complex Tasks".
American Journal of Psychiatry, 138:1441, 1981, "Psychomotor Function in Affective Disorders ...".
New England Journal of Medicine, 306:1496, 1982, "Lack of Interpersonal Communication in Programmed Learning".
Science, 217:925, 1982, "The Clocks that Time Us" by Moor-ede, Sulzman and Fuller, Howard University Press, 1982.
Science, 217:79, 1982.
Medical Tribune, p. 1, Nov. 10, 1982.

(List continued on next page.)

Primary Examiner—Kyle L. Howell
Assistant Examiner—Francis J. Jaworski
Attorney, Agent, or Firm—Pearne, Gordon, Sessions, McCoy, Granger & Tilberry

[57] ABSTRACT

Responses of a human subject may be by voice, hand or foot movement, or bodily secretions, as examples. A hiatus of such responses may be termed a lapse in the continuity of the response, including a hesitation pause in the voice, a movement of hand or foot on a monitored control of a motor vehicle or vehicle simulator, or pulsatile bodily secretions on a monitored control of an implantable insulin pump. In a voice response, the hesitation pause may be more than about one second in the voice of a subject during a dialogue or monologue. The hiatus rate of such responses is indicated by the present apparatus, as is the average hiatus duration for two or more hiatus rates. The dominant hiatus rate is also determined and indicated. A microprocessor is utilized in such determination. The foregoing abstract is merely a resume of one general application, is not a complete discussion of all principles of operation or applications, and is not to be construed as a limitation on the scope of the claimed subject matter.

49 Claims, 21 Drawing Figures

OTHER PUBLICATIONS

*JAMA*, 1983; 249:54-59, "Effects of Stress Management Training and Dietary Changes in Treating Ischemic Heart Disease".

N. Engl. J. Med., 307:1476, 1982, "Behavioral Treatment for the Anticipatory Nausea and Vomiting Induced by Cancer Chemotherapy.

*Psychiatric News*-Nov. 19, 1982, "Severity of Post-Stroke Depression Relating to Location of Brain Injury," Study Shows.

*Am. J. Psychiatry* 139.8, Aug. 1982, "Verbal Behavior: Adaptation and Psychopathology".

*QR The Quieting Reflex*—Charles F. Stroebel, New York G. P. Putnam's Sons, 1982.

*New York Times*, "Patents: Classroom Computer Monitor", Feb. 26, 1983.

*Language and Speech*, 5:31, 1962.

*Am J. Psychiatry*, 140:265, 1983.

*Arch. Psychiat.*, Nov., 225:209, 1978.

*Science*, 217:1223, 1982, "Some Effects of Disconnecting the Cerebral Hemispheres" by Roger Sperry.

*The Journal of American Medical Association*, 248:1465, 1982, "Multiple Risk Factor Intervention Trial".

*Medical Tribune*, vol. 23, No. 20, Sep. 29, 1982, "Deliver Drugs by Pump on Command", pp. 1, 20.

*Medical Tribune*, vol. 23, No. 20, Sep. 29, 1982, "Driving Under the Influence of 'Pot' . . . ", pp. 3, 12.

*Clinical Psychiatry News*, Oct. 1982, "Call for Focus on Motivating Change in Life-Styles", p. 18.

*Circulation*, Supple. VI, vols. XXXVII & XXXVIII, Oct. 1968, "Glucose Tolerance & the Control of Aggression in Middle-Aged Businessmen", p. VI-79.

*Circulation, Supple. II, vols. XXXV & XXXVI, Oct. 1967*, "Coronary Risk Factors . . . ", p. II-113.

*Glucose Tolerance and the Control of Aggression*", (present at annual meeting of The American Psychiatric Association, May 7, 1969).

"*Influence of Stress on Lipid and Carbohydrate Metabolism*" by E. H. Friedman in Thrombosis, Eds. Brinkhous, K. M. et al., Stuttgart-New York: F. K. Schattauer Verlag, 1972, pp. 67-78.

*Medical Tribune*, Apr. 13, 1983, "Is Frontal Pole Damage Key to Post-Stroke Depression".

*Medical Tribune*, May 11, 1983, "Avert 15,000 2d MIs a Year Behaviorally".

*Medical Tribune*, May 11, 1983, "A,B Typology Challenged by Study; Findings Rebutted by Dr. Friedman".

*The Lancet*, Nov. 20, 1982, "Type A Behaviour: Not Specifically Pathogenic?".

*Psychiatric Capsule & Comment*, May 1983, pp. 5 and 6.

*Clinical Psychiatry News*, May 1983, "Some Type A's May Not be at Increased Risk of C-V Disease".

*Reflections of Reality in Japanese Art*, "Portrait of the Zen Priest Ikkya Sojun", pp. 10 and 11.

*Psychosomatic Medicine*, vol. 44, No. 6, (Dec. 1982), "The Effects of Normal and Rapid Speech on Blood Pressure".

*Science*, 220:733, "Social Stress and Atherosclerosis in Nomocholesterolemic Monkeys", May 13, 1983.

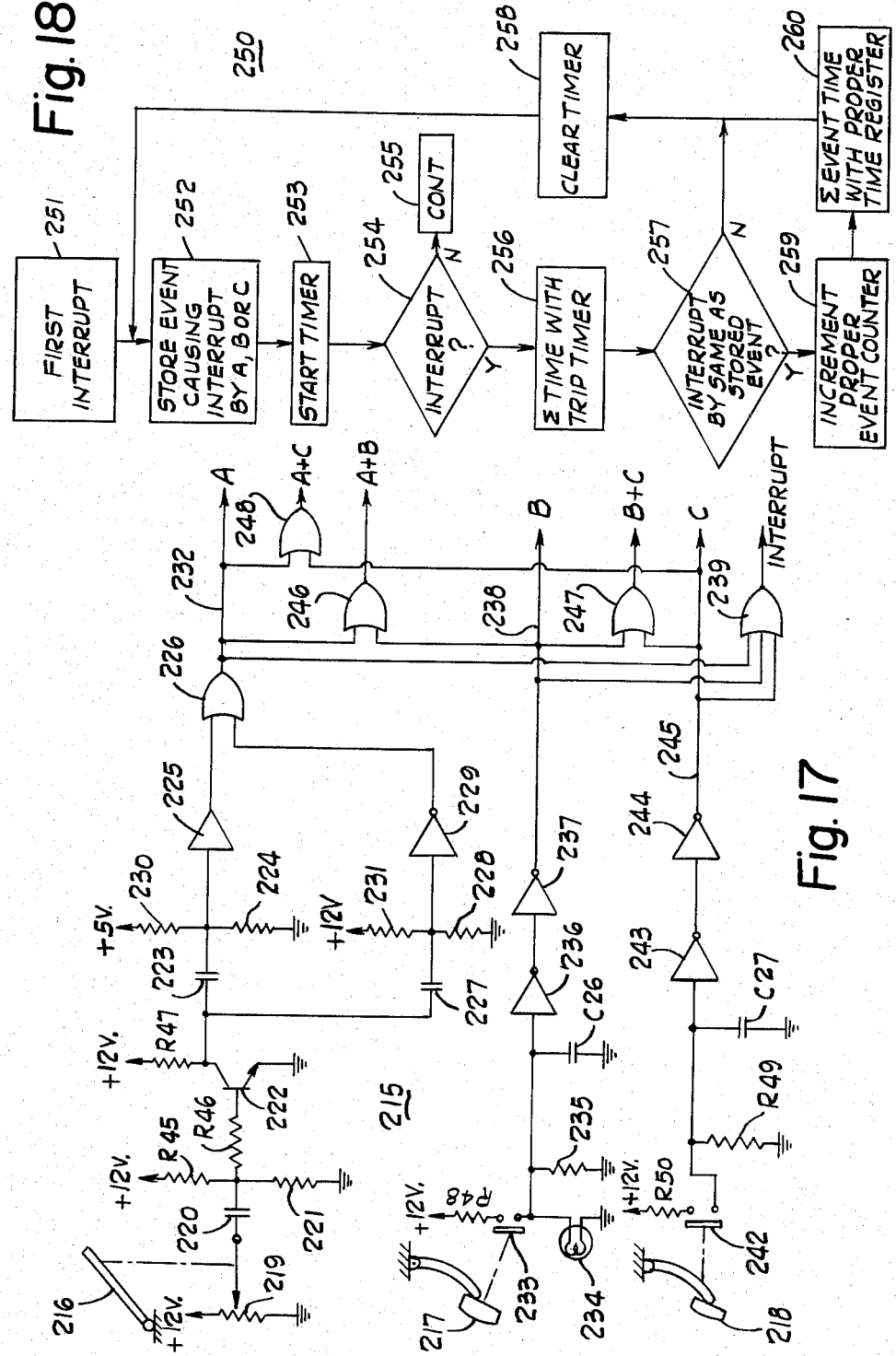

HUMAN RESPONSE APPARATUS AND METHOD

PRIOR ART

Only a few prior patents have disclosed apparatus to be responsive to hesitation pauses in human speech. The West German patent No. 1,123,431, patented Sept. 6, 1962, relates to a person speaking in a monologue and speaking continually perhaps for 30 minutes. Time signals are produced at intervals of one-half second as an example. A register $Z_s$ registers the total time of the monologue speech and a register $Z_p$ registers the total time of all of the pauses in this monologue speech, which pauses are in excess of 0.5 second duration. Thus, in a 30-minute speech, register $Z_s$ might register 29 minutes and 5 seconds of speech, and register $Z_p$ might register 55 seconds of total pauses. A comparison device R1 produces a quotient of the numbers in these two registers, which would be 31.72 or 0.0315, for example, depending on which is the divisor.

U.S. Pat. No. 4,156,423 to Ernest H. Friedman et al. disclosed a method to diagnose coronary atherosclerosis. Apparatus was disclosed which determined the number of hesitation pauses of joint silence of two persons having a dialogue, bounded by speech uttered by the subject, which pauses were in excess of a time interval in the order of one second of time. The apparatus disclosed red, yellow, and green lights to indicate different rates of hesitation pauses of the subject, the red light being illuminated upon occurrence of greater than 2 pauses per minute, thus giving an indication of the subject's proneness to clinical coronary atherosclerosis. U.S. Pat. No. 4,278,096 had a similar disclosure, and added switching means to the apparatus, so that either the local or the distant voice could be the voice of the subject under analysis.

Behavioral counseling, including correction of speech dysrhythmia utilizing videotaped visual feedback, has been found to be more effective than cardiologic counseling in preventing nonfatal myocardial infarction in postcoronary patients. The combination of the two interventions was more effective than no counseling, as reflected in the rates of infarction and cardiovascular death. A prospective randomized study by Meyer Friedman et al. (*Circulation* 66:83, 1982) followed 1,035 subjects. Over a five-year period, both morbidity and mortality outcome criteria demonstrated the value of creating awareness for change of specific coronary-prone behavior. Also see *Science* 218, 31, 1982.

U.S. Pat. No. 3,818,609 relates to interactive paired learning by a learner pair at a work space with a stimulus field such as a CRT being able to respond so that each of the pair learns more quickly than if each were studying alone. A method described in U.S. Pat. No. 4,375,080 requires an observer in the classroom to punch a computer-connected keyboard to select and time various classroom activities, e.g., questions and responses between teacher and students. *New York Times,* "Patents: Classroom Computer Monitor" Feb. 26, 1983. Meyer Friedman et al. utilized a similar approach by having high coronary-prone subjects observe and model their behavior after low coronary-prone individuals. The dual display in the present application allows hesitant individuals to model themselves after conversational partners by comparing and contrasting degrees of fluency and prosody. This method has particular application in focused interpersonal staff training programs in organizational development. On an intrapersonal level, contrasting adaptive (relaxation) responses counter-conditioned to maladaptive (nausea and vomiting) responses are effective in desensitizing patients with anticipatory nausea and vomiting induced by cancer chemotherapy. The patient while relaxed imagines specific scenes just prior to treatment (New England Journal of Medicine 307:1476, 1982).

Stress management, including visualizing atherosclerotic plaques being removed from the coronary arteries, coupled with dietary intervention, resulted in a 44% mean increase in duration of exercise, a 55% mean increase in total work performed, somewhat improved left ventricular regional wall motion during peak exercise, a net change in the left ventricular ejection fraction from rest to maximum exercise of +6.4%, a 20.5% mean decrease in plasma cholesterol levels, and a 91.0% mean reduction in frequency of anginal episodes (JAMA 249:54, 1983).

Another intrapersonal technique is QR The Quieting Reflex, a six-second technique which includes a mental pause to shift from a left brain mode which overdrives the body to a right brain mode which is involved in more creative functioning. Confirmation of having achieved the quieting reflex is based on subjective experience of bodily sensations. Objective measurements of the effect of the quieting reflex on slowing left brain function and permitting access to the right brain are in process and are yet to be reported. (*QR The Quieting Reflex,* by Charles F. Stroebel, New York. G. P. Putnam's Sons, 1982).

Computerized educational techniques have been cited by Dr. Edmund J. Lewis (New England Journal of Medicine 306:1495, 1982) as isolating the student from interpersonal communications. This can lead to individuals who are limited in conducting social intercourse and thus isolated and hostile. Using a computerized method to enhance rather than stultify interpersonal skills is desirable, both on the telephone and in face-to-face interaction, utilizing voice print technology in the classroom and in one-on-one situations by way of a dual voice fluency display incorporated in a wristwatch. The last embodiment is shown in U.S. Pat. No. 4,351,983, which discloses a method of distinguishing between voice and other sounds. It is an example of a complex prior art system compared to the method used in the present invention.

Dr. Elliott D. Ross's article, "The Divided Self," on pages 8-12 of *The Sciences* for February 1982 refers to the right and left hemisphere of the brain and to Broca's Area of the brain which, if damaged, results in Broca's aphasia, which impairs the patient's ability to speak fluently, although he can still comprehend the speech of others. Wernicke's area is likewise on the left hemisphere of the brain, although when this area is damaged the patient remains able to speak, using words and grammar fluently but experiencing difficulty comprehending the speech of others. Ross refers to areas on the right half of the brain corresponding in position to Broca's and Wernicke's area which, if damaged, result in (1) the patient's ability to speak fluently but without any gestures or any prosodic variations that convey emotions, and (2) the patent's ability to understand speech but to be unable to understand emotions or moods, such as happiness, anger, or despondency, conveyed by such speech of the other person, respectively. Thus, Ross concludes that there is a definite interaction between the right and left hemispheres of the brain, the left hemisphere controlling the language functions of the speech and the right hemisphere controlling the emotional quality or prosody of the speech.

Dr. Elliott Ross expands on his thesis in an article in *Clinical Psychiatry News*, July 1982, at pp. 3 and 16. The right hemisphere is the origin of endogenous depression, a cardinal symptom of which is elongated pause duration. The severity of the depression increases the closer to the front of the left brain a stroke occurs, according to Dr. Robert G. Robinson in *Psychiatric News*, Nov. 19, 1982, at pp. 5 and 10. These data support evaluation of severity and type of depression by monitoring both hemispheres; the frequency of pauses governed by Broca's area on the left and duration of pauses determined on the right. In the experience of Ernest H. Friedman, M.D., a typical endogenously depressed patient will pause at a rate that is consistently greater than two times per minute. In this dysfluent mode, pause duration will decrease with drug treatment in a stepwise manner from 2.22 seconds on admission to a hospital to 1.90 seconds on day 12 to 1.73 on day 16, which is within one standard deviation of the mean of 1.50 seconds standard deviation of 0.33 seconds determined in 500 monitoring records previously obtained. The validity of this observation is confirmed by the prior report of Szabadi et al. (cited in U.S. Pat. No. 4,156,423) and confirmed and extended by Greden and Carroll (*American Journal of Psychiatry* 138:1441, 1981) demonstrating a similar phenomenon and by the fact that antidepressant drugs have a characteristic two-week start-up time. During this two-week period, pause duration serves as an objective guide to adjusting the dosage of medication. Charting the patient's pause duration in a red (unsatisfactory) mode as one would a temperature curve provides an immediate perception of diurnal patterns, since depressive patients frequently exhibit longer pauses in the morning compared with the afternoon (Greden and Carroll) and change over the entire hospital course. This longitudinal picture allows one to use the individual's own baseline duration as a basis for later comparison as described by Szabadi et al. and Greden and Carroll. Frequency of elongated pauses is higher in patients with organic brain lesions and in depression than in mania. *Arch. Psychiat*, November 225:209 1978.

Diurnal variation of speech pause duration in an endogenous depression (longer pauses in the morning and shorter pauses in the afternoon; difference greater than one standard deviation of 0.33 seconds), as described by Greden and Carroll, is an example of utilizing recently gained knowledge of biological rhythms for the benefit of human health.

Smaller quantities of speech in depressive individuals can be measured by speech time as a percent of the total conversation. (*Verbal Behavior: Adaptation and Psychopathology*, by Walter Weintraub. New York. Springer Publishing Co., 1981)

Weintraub has demonstrated that frequent long pauses are indicative of anger in men and women in both uninstructed and instructed interviews under simulated conditions, p<0.01. This is congruent with the psychoanalytic view of depression as retroflexed anger. However, a psychophysiological basis is a more likely explanation for decreased speech productivity and long and frequent silences in severe depressives during unstructured clinical interviews.

An object of this invention is to motivate physicians at least to begin to consider circadian rhythmicity in their practices. Evaluation of circadian rhythmicity in the classroom using voice print technology is a new method for screening for early intervention in mood disorders. *The Clocks That Time Us*, by Moor-ede, Sulzman and Fuller, Harvard University Press, 1982; and *Science* 217: 925, 1982.

Impairment of driving skills has been found due to use by the driver of the drug diazepam, resulting in increased difficulty in keeping the vehicle in a single lane of a highway. *Science*, 217:79, 1982. Also, some vehicle drivers, such as truck drivers, should have regular physical examinations to determine fitness to drive. Lack of proper medical examinations can lead to accidents by medically unfit drivers, including those who should be taking insulin for diabetes, *Medical Tribune*, page 1. Nov. 10, 1982.

An article by Ernest H. Friedman, M.D. entitled "Stress and Intensive Care Nursing: Ten-Year Reappraisal" printed in *Heart & Lung: The Journal of Critical Care*, St. Louis, Vol. 11, No. 1, pp. 26–28, January–February 1982, relates to this subject. It suggests that nurses working in intensive care units of a hospital should develop communication skills to meet the daily demands of their patients in the work place. The original article, entitled "Stress and Intensive Care Nursing" and published in *Heart & Lung* November–December 1972, Vol. 1, No. 6, pp. 753–754, related to this same general subject.

A similar disclosure to that of U.S. Pat. No. 4,278,096 is found in copending patent application Ser. No. 230,725 of Friedman et al., filed Feb. 2, 1981, entitled "Method and Monitor for Voice Fluency."

An article in *Psychiatric News*, Aug. 6, 1982 reports on a speech given by Peter Wolff, M.D. relating to "Brain Hemispheres Function As A Unit In Complex Tasks." The speech discussed the right and left hemispheres of the brain and manual functions in humans. Longer, less frequent hesitation pauses are associated with better verbal planning and correlate positively with social class. *Language and Speech*, 5:31 1962. Frequent elongated pauses are a unique neuromotor indicator of depression. *AM J. Psychiatry* 140:265 1983. Thus, pause durations must be examined on a time base to determine their adaptive significance.

SUMMARY OF THE INVENTION

The present invention relates to human neuromotor response, such as speech, keystrokes on a computer terminal, or steering wheel and pedal actuation in a motor vehicle or vehicle simulator, for example. It also relates to a human response such as bodily secretions. Apparatus and a method are disclosed for determining and displaying hiatus frequency and duration. A hiatus is a lapse in the continuity of the human or neuromotor response. If a response is a voice response, a hiatus is defined as a timed interruption in the response, the average rate of hesitation pauses being measured in a given time segment, and these hesitation pause rates are sorted into at least two levels or frequency bands, and finally, there is an indicator to indicate to human sensors for transmission to the brain the dominant hiatus or hesitation pause level and the average hiatus or pause duration for each level. This determination and display may be used by the health caretaker, trainer, or teacher, or the individual himself, in several ways. It may be used to assess and coordinate the left and right cerebral hemisphere interactions; it may be used to diagnose endogenous depression; it may be used to modify coronary-prone behavior; and it may be used as an aid in approximating the pace of the conversational partner. The apparatus utilizes microprocessor technology to determine pause frequency and pause duration, and has a dual display of the pause durations and frequency of each of two persons having a dialogue.

A feature of the present invention is that a multiple display is provided. This permits neuromotor response comparison, namely neuromotor efficiency at two or more levels, by comparing responses of two or more interacting individuals or two or more similar responses by one individual. The neuromotor response may include vocal fluency and an end result can be the potential use in organizational development to teach communication skills in staff training. This can be a comparison of one person with another, and hence would be interpersonal interaction.

Another potential use is in evaluating handedness in terms of finger dexterity, e.g., right hand versus left hand, and utilizing keyboards similar to typewriter keyboards, wherein the right-handed dexterity is compared with the left-handed dexterity. This is intrapersonal evaluation. The utility is to diagnose handedness to discover imbalance that may be corrected with training.

Other intrapersonal comparisons are neuromotor responses between the hands, e.g., steering wheel and the right and left feet of a person, e.g., the accelerator, brake, and clutch controls on a motorized vehicle. This has utility for driver training in a simulator; and on-line monitoring in a motor vehicle by transmission via radio frequency to a control monitor, and retrospective evaluation, as in a "flight recorder." It has usefulness in developing the driver's contribution to fuel efficiency by minimizing pumping the accelerator and limiting the use of the brake. It also may be used to measure driver efficiency in terms of mental depression and coronary-prone behavior, e.g., suicide and susceptibility to heart attack at the wheel of the vehicle. If the multiple display is utilized as a method of driver training, it may be presented after the trip is completed upon turning off the ignition so as not to distract the driver enroute.

The apparatus and method permit the evaluation of four different factors:

(1) the dominant or average frequency level of the hiatuses or hesitation pauses, which may be indicated by a voice synthesizer or illumination of red, yellow, or green indicator lights, a green light indicating high efficiency as the desired response.

(2) the peak efficiency level, which is shown by an indicator such as a digital readout juxtaposed to these lights.

(3) a measure of the flexibility of the speech pattern of the subject so that a determination can be made as to how the hesitation pattern may be changed by modifying the pause durations in each of the three frequency ranges. As in all servocontrol mechanisms, the output is constant, namely, frequency times duration is a constant. The therapeutic benefit is by having patients see how increasing pause duration allows adequate time to collect thoughts, thus leading to a decreased rate of speech hesitation. Decreasing pause frequency by increasing pause duration results in melodic speech or prosody, a right brain function.

(4) a dual display for indication of how the subject corresponds in speech fluency and prosody with another person.

An analysis of over 500 dialogues indicates that hesitation pause durations have a mean of about 1.50 seconds with a standard deviation of 0.33 second. Accordingly, the present apparatus and method permit a means of identifying hesitation pause durations at high, middle, and low coronary risk (U.S. Pat. No. 4,278,096) and matching of dominant pause durations in a dual display format to determine interpersonal harmony of pace at the 95 percent level of confidence. This 95 percent level of confidence may be defined as the probability P being less than 0.05 discordance, namely, there being only one chance in 20 that a person is classified in one group when he should actually have been classified in the other group.

When speaking with a dysfluent person, the instrument user especially strives to attain a match by achieving higher fluency, e.g., green versus yellow or red light, or yellow versus red light. This provides a balance or a model for the dysfluent conversational partner. An even closer approximation or similar directional change of pause durations at higher fluency levels immediately adjacent to the dominant modes is indicative of adaptive interpersonal interaction.

The problem to be solved, therefore, is how to construct apparatus and how to utilize a method of determining pause frequency and pause duration of a human neuromotor response.

The problem is solved by a computing device for evaluation of human response, comprising in combination, input signal receiving means operable to receive first type signals from a signal generator of at least a first human subject, means to measure the elapsed time between consecutive signals from said human subject, means for sorting said elapsed times into at least two frequency levels, computing means to determine the average elapsed time of each of said levels, and recording means operable to record on a time base the dominant frequency level and the average elapsed time of each level for at least said first human subject.

The problem is further solved by a human response system for determining the hiatus rate of a neuromotor response of a human subject, comprising in combination, transducer means responsive to at least one neuromotor response of the subject who is subjected to sensory inputs to the right and left hemispheres of the brain, hiatus means connected to said transducer means to determine the occurrence of a hiatus in a predetermined neuromotor response of the subject defined as the absence of all monitored neuromotor responses for a predetermined time interval bounded by the predetermined neuromotor responses, rate means connected to said hiatus means to determine the average hiatus rate in a given segment of the predetermined neuromotor response of the subject, sorting means to sort the hiatus rates into at least two levels of response, and means to indicate the average time duration of the individual hiatuses for each of the two rate levels.

The problem is also solved by apparatus for determining human response patterns of a human subject, comprising in combination, transducer means responsive to at least one human response of the subject, hiatus means connected to the transducer means for determining a hiatus in the human response of the subject defined as the absence of all monitored human responses for a predetermined time interval bounded by responses of the predetermined neuromotor, rate means for determining the rate of the successive hiatuses, means to sort the hiatus rates into at least two levels, and output means connected to the sorting means and having an output to represent at least one level of hiatus rates, characterized in that the output means is responsive to both the dominant level and the average hiatus duration of such level.

The problem is also solved by an information feedback voice monitoring system, comprising in combination, transducer means connected to be responsive to the voice of a subject and to another voice with whom the subject may have a dialogue, a control circuit connected to said transducer means, means in said control circuit to determine the occurrence of a hesitation pause in the speech of the subject, which hesitation pause is defined as a joint silence of one second or more bounded by the speech of such subject during a dialogue, means in said control circuit to determine the frequency of hesitation pauses in the speech of the subject during a dialogue with another person, a sensory output having signal codes of satisfactory, caution and unsatisfactory associated with a numerical indication of the time duration of the pause, and a microprocessor connected to the output of said pause and frequency determining means and having an output to said sensory output to emphasize only one signal code of satisfactory, caution or unsatisfactory, depending on the number of pauses per minute being 0 to about 1.5, about 1.5 to 2, and more than 2, respectively, and to indicate the average time duration of those hesitation pauses which fall within the pause per minute range of 0 to about 1.5, about 1.5 to 2, and more than 2, respectively.

The problem is further solved by a voice monitoring system for determining the voice fluency of a human subject, comprising in combination, transducer means responsive to the voice of the subject and to another voice with whom the subject may have a dialogue, pause means connected to said transducer means to determine the occurrence of a hesitation pause in the voice of the subject defined as a pause of a time duration longer than in the order of one second of joint silence of both voices bounded by the voice of the subject, rate means connected to said pause means to determine the average rate of hesitation pauses in a given voice segment of the subject, sorting means to sort the hesitation rates into at least two levels of fluency, and means to indicate the average time duration of the individual hesitation pauses for each of the two levels.

The problem is also solved by the method of determining hiatus frequency and duration of a human neuromotor response, comprising in combination, determining the occurrence of a hiatus in the neuromotor response of a subject defined as a lapse in the continuity of the response, measuring the average hiatus rate in a given time segment of a response, sorting the hiatus rates into at least two levels, and indicating to human sensors for transfer to the brain the dominant level and the average hiatus duration of each level.

The problem is further solved by the method of determining a human subject's pause frequency and pause duration while having a dialogue, comprising in combination, measuring the length of pauses in the speech of the subject bounded by speech of the subject and establishing such pause as a hesitation pause when the length thereof exceeds about one second of time, determining the rate of hesitation pauses in the speech of said subject while having a dialogue, assigning a satisfactory code to those hesitation pauses in the speech of said subject which occur after more than about one minute of speech without a hesitation pause, assigning a caution code to the second hesitation pause which occurs during any one minute of the dialogue, activating a caution indicator indicating an average of about one to two hesitation pauses per minute, and determining and displaying the average time duration of the dominant one of the satisfactory and caution code pauses for said subject.

Accordingly, an object of the invention is to provide apparatus and method for determining, storing and displaying hiatus frequency and hiatus duration of a human neuromotor response.

Other objects and a fuller understanding of the invention may be had by referring to the following description and claims, taken in conjunction with the accompanying drawings.

BRIEF DESCRIPTION OF THE DRAWINGS

FIG. 17 is a schematic diagram of a modification determining response of pedal actuation in a motor vehicle;

FIG. 18 is a flow chart of the operation of the microprocessor when used with the circuit of FIG. 17;

DETAILED DESCRIPTION OF THE PREFERRED EMBODIMENTS

Figure 1:
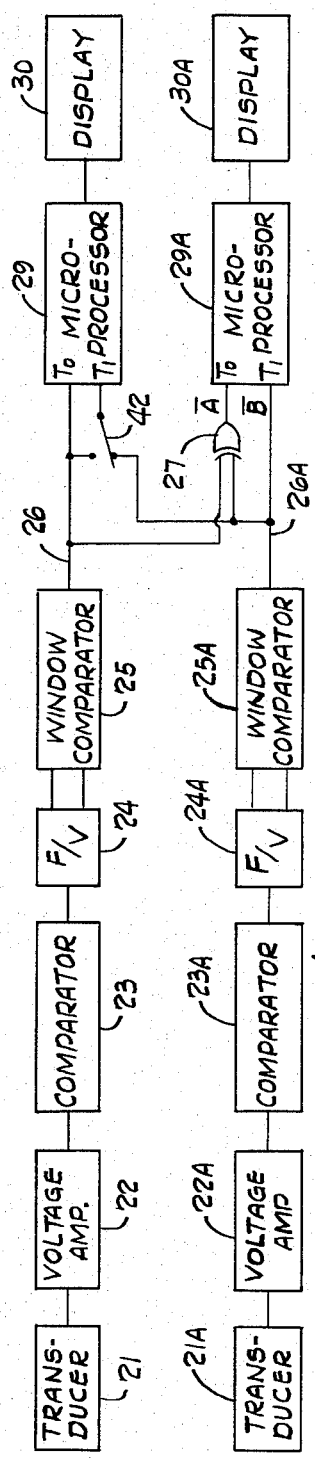
FIG. 1 is a block diagram of a human neuromotor response circuit in accordance with the invention.

FIG. 1 illustrates a block diagram of the present invention, which determines human response and, more particularly, neuromotor response. In one form of the invention, the neuromotor response may permit comparison, either interpersonal or intrapersonal, by means of a dual display, and this dual display is illustrated in FIG. 2.

The neuromotor response apparatus 10 shown in FIG. 1 includes a transducer 21, which may be any form of transducer of the neuromotor response, either an analog or a digital transducer. In this FIG. 1, the transducer 21 is shown as a microphone having an output fed to a voltage amplifier 22 to amplify the signal level, and then it is passed to a comparator 23, which saturates and forms square-topped pulses. This helps to distinguish over interfering noise and makes essentially a pulse train. This pulse train is then passed to a frequency-to-analog converter, shown as a frequency-to-voltage converter 24, and the voltage signal therefrom is passed to a window comparator 25. This window comparator 25 limits band width to the fundamental components of human speech. The signal is passed on a line 26 to a microprocessor 29, which processes the signal in accordance with a predetermined program, and the information is then passed to an output or display unit 30.

The neuromotor response apparatus 20 permits not only a single display or output, but also a dual display or output, and to accomplish this, the elements 21–26, 29, and 30 referred to above are duplicated in FIG. 1, and shown with the letter A suffix. Additionally in FIG. 1, it will be noted that the line 26 feeds not only the microprocessor 29, but also feeds one input of an exclusive OR gate 27. Line 26A supplies the microprocessor 29A, the microprocessor 29 through a switch 42, and the other input of the exclusive OR gate 27. The output of this gate is supplied to the microprocessor 29A. This allows the same program to be used by the dual display 30 through logical switching.

Figure 2:
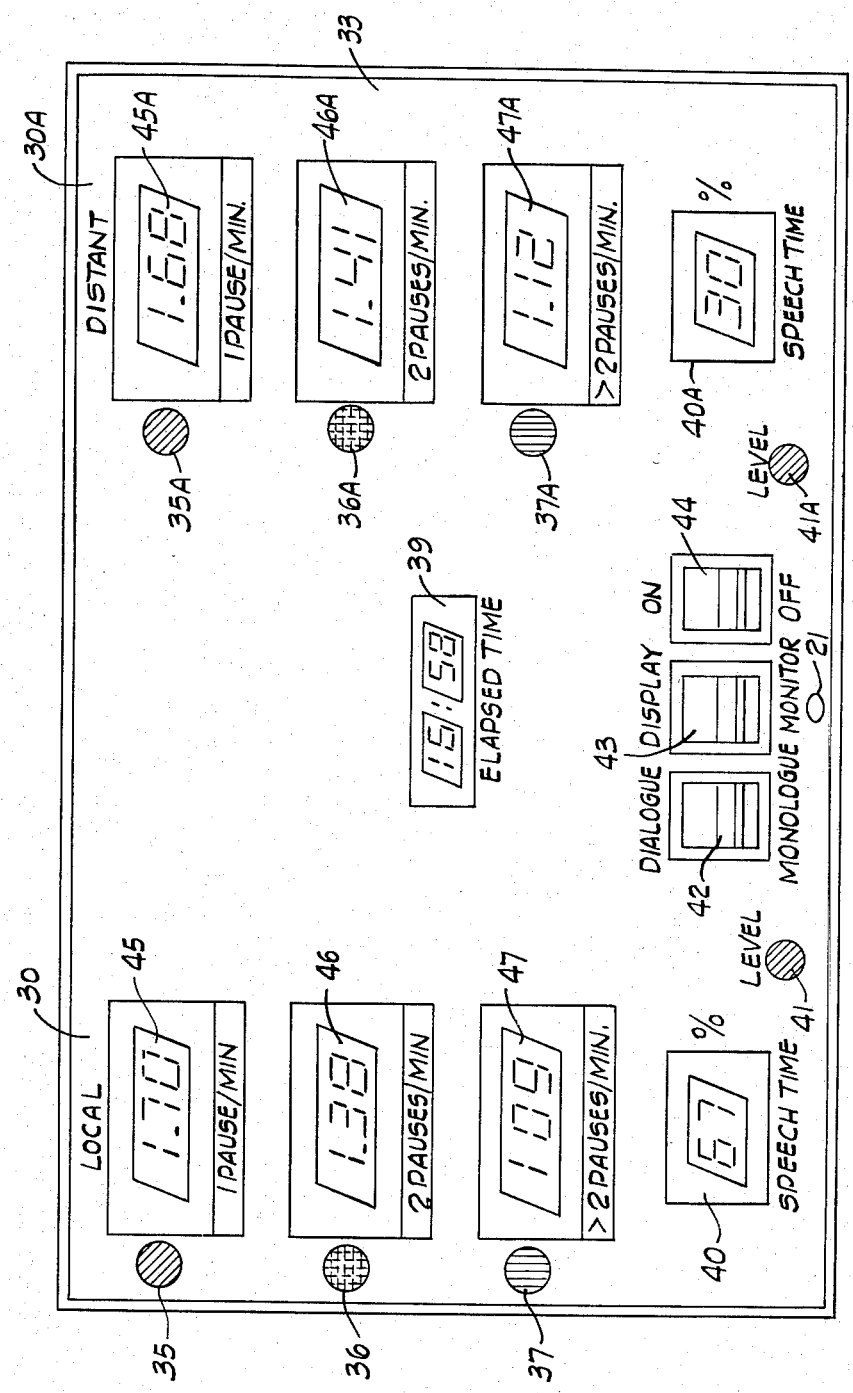
FIG. 2 is a plan view of the front panel of apparatus embodying the invention.

FIG. 2 illustrates a display panel 33 which incorporates the output unit as a recording or display unit 30 on the left and a recording or display unit 30A on the right. This particular display panel 33 is adapted for neuromotor responses which are the voices of two persons, namely an interpersonal interaction, and one feature of the present invention is that it may be utilized with a telephone so that the display unit 30 displays the local voice response and the display unit 30A displays the distant voice response. It may also be used with other interpersonal communication, e.g., units such as keyboard units with the local keyboard inputs displayed on the left and the distant keyboard inputs displayed on the right. Still further, it may be utilized for intrapersonal interaction, e.g., neuromotor response of actuation of pedals on a motor vehicle or vehicle simulator, with the left foot neuromotor response displayed on the left display panel 30 and the right foot neuromotor response displayed on the right half display 30A. It may be used also as a single display of responses to a steering wheel of a motor vehicle or vehicle simulator, or a dual display of responses to a motor vehicle steering wheel plus responses on a vehicle pedal, e.g., the accelerator.

The present apparatus is capable of determining the occurrence of a hiatus or hesitation pause in the human or neuromotor response of a subject, and this is defined as the absence of all monitored human or neuromotor responses for a predetermined time interval bounded by the predetermined response. When the response is a voice response, it may be defined as a timed interruption in the response of such subject. The timed interruption may be in the order of one second of time. Also, the apparatus is capable of measuring the average hiatus rate in a given time segment of a response. If, for example, a person is engaged in a dialogue with another person or a computer (either a voice or keyboard dialogue), the number of hesitation pauses in total conversation will determine the average rate of such hesitation pauses. The apparatus is capable of sorting these hesitation pause rates into at least two levels of fluency, and FIG. 2 shows the display panel 33 as having three different levels or rates of hesitation pauses. A green lamp 35 may be illuminated if the hesitation pause rate is about one pause per minute, or less; a yellow indicator lamp 36 may be illuminated if the hesitation pause rate is between about one and two pauses per minute; and a red indicator lamp 37, as part of an output indicator 38 (FIG. 6), may be illuminated if the hesitation pause rate is in excess of about two pauses per minute. Similar green, yellow, and red indicator lamps 35A, 36A, and 37A are provided on the right half display unit 30A. An elapsed time indicator 39 is provided to indicate the time of the entire communication. A percent speech time indicator 40 and 40A indicates the percentage of the total time that each of the two individuals is speaking or communicating. A green level indicator lamp 41 is illuminated if the local voice is speaking loudly enough so that a microphone transducer 21 obtains a satisfactory input level. A similar green indicator lamp 41A for the distant voice indicates whether a satisfactory signal level is being received from such distant voice. Switches 42, 43, and 44 are also provided on the display panel 33 to control a dialogue/monologue mode, a display/monitor selector switch, and an ON/OFF control.

The green, yellow, and red indicator lamps 35, 36, and 37 provide a sensory output of satisfactory, caution and unsatisfactory rates of hesitation pauses in the communication of each of the two persons. Additionally, juxtaposed to these indicator lamps are digital readouts 45, 46, and 47, respectively. These give a sensory output to the eye of the observer of the average duration of the hesitation pauses in each of the three levels or rates of hesitation pauses. Similarly, digital readouts 45A, 46A, and 47A are juxtaposed to the green, yellow, and red indicator lamps 35A, 36A, and 37A, respectively, for a similar purpose.

Figures 3, 4:
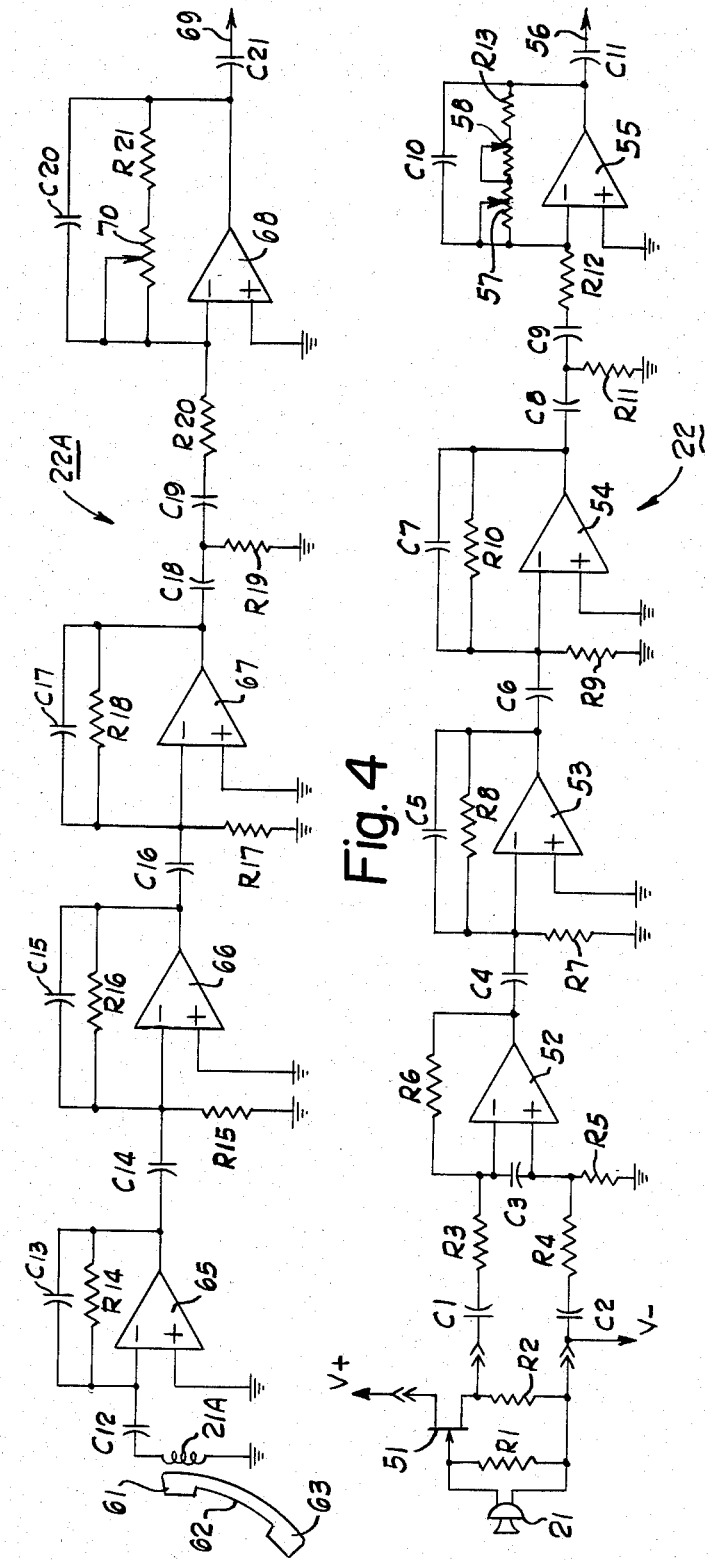
FIG. 3 is a schematic diagram of a preferred voltage amplifier circuit for a microphone pickup.
FIG. 4 is a schematic diagram of a preferred form of a voltage amplifier circuit for an inductive pickup.

FIG. 3 illustrates a portion of the neuromotor response apparatus 20 in a preferred embodiment of a voice responsive apparatus. More specifically, FIG. 3 illustrates the voice amplifier section 22 shown in the block diagram of FIG. 1. This voice amplifier 22 has an input from the transducer 21, which in this case may be a microphone such as an electret microphone having a capacitive effect. The signal is buffered by an FET transistor 51, and further amplified in operational amplifiers 52, 53, 54, and 55. The electret microphone does not have a high level output, so several stages of gain are desirable, and each stage acts as a filtering stage in addition. This means that the voice signal changes from complex sine waves with harmonics to one which is more nearly a pulsatile wave by the amplifying and clipping action of these several amplifier and filter stages, and band limited to the 300 to 3000 Hertz range for a human voice. Therefore, when the signal is presented at an output conductor 56 at the end of the chain of amplifiers, it is essentially a pulse train. Potentiometers 57 and 58 provide fine and coarse gain adjustment.

FIG. 4 is a schematic diagram similar to that of FIG. 3, and illustrates the circuit which may be used in the voltage amplifier 22A of FIG. 1 when such voltage amplifier is used with a voice responsive circuit. The circuit of FIG. 4 may be utilized with a telephone, with the transducer or microphone 21 responsive to the local voice and transducer 21A responsive to the remote voice. In FIG. 4, this transducer 21A is shown as an inductive pickup located adjacent to the earpiece 61 of a telephone 62. The mouthpiece 63 of this telephone 62 would receive the local voice, and this local voice would actually be received both in the microphone 21 on the display panel 33 of FIG. 1 and on the inductive pickup 21A adjacent the earpiece 61. This reception of the local voice signals on both the microphone 21 and the inductive pickup 21A, reception of only the remote voice signals on the inductive pickup 21A, with noise on both yet discrimination between the two voices, is accommodated by the present neuromotor response apparatus 20.

In the voltage amplifier 22A, the inductive pickup 21A supplies a signal which is amplified by Op/Amps 65, 66, 67, and 68, with the Op/Amp 68 supplying an output conductor 69 and being controlled in gain by a potentiometer 70. Again, the four Op/Amp stages act as combined filtering stages, so that essentially a pulse train output is presented to the output conductor 69 at a voice frequency.

Figure 5:
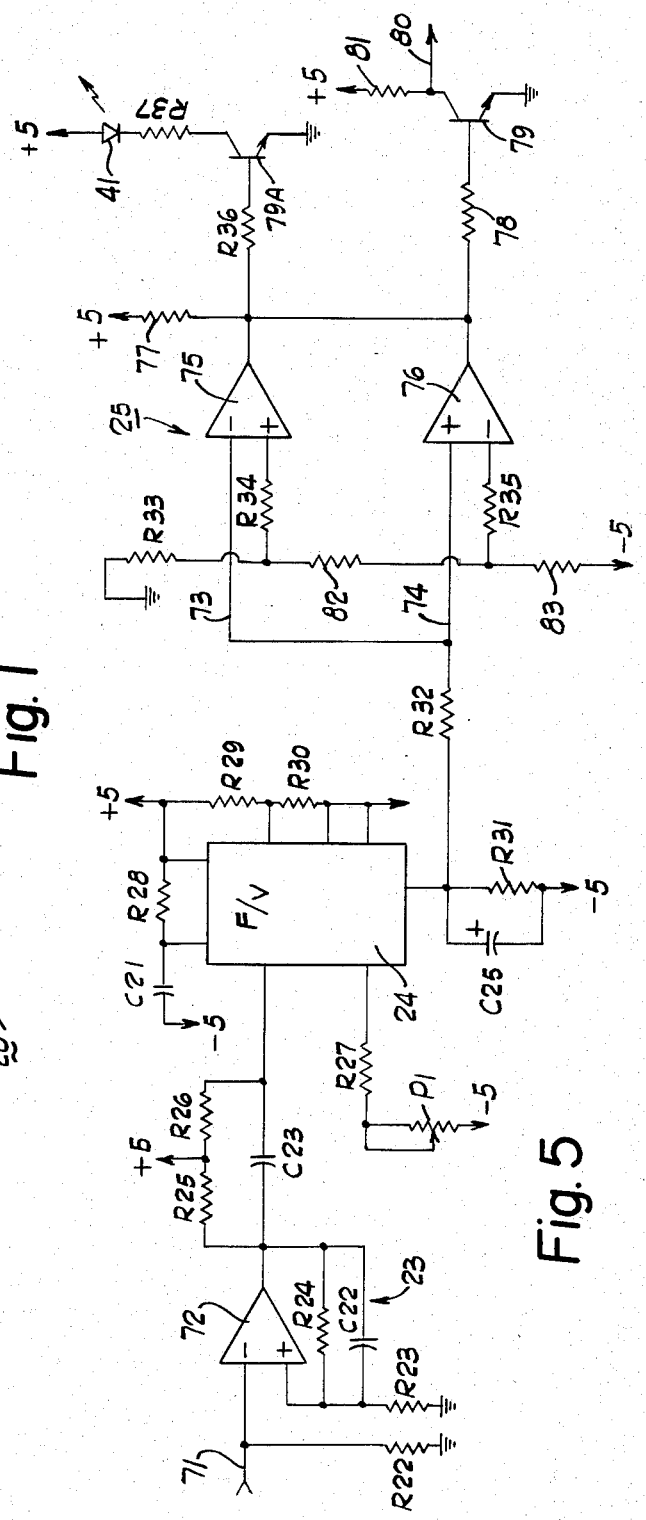
FIG. 5 is a schematic diagram of the preferred form of comparator, frequency-to-voltage converter, and window comparator of FIG. 1.

FIG. 5 illustrates schematically the components of the comparator 23, frequency-to-voltage converter 24, and window comparator 25 shown in FIG. 1. The circuit of FIG. 5 is duplicated in FIG. 1 so that the same type of components are used for the parts 23A, 24A, and 25A. FIG. 5 shows an input conductor 71 which will receive an input from either the output conductor 56 or the output conductor 69. This input conductor 71 supplies a signal to an Op/Amp 72, which is the type of Op/Amp which has an open collector and is configured as a comparator in its comparing with the ground level. The output of this Op/Amp 72 is truly a square-topped pulse train signal at a frequency which includes the voice range of 300 Hertz to 3 kilohertz. The output is fed to a frequency-to-voltage converter 24, which has an output at 73 and 74 to the window comparator 25. This window comparator comprises Op/Amps 75 and 76. The purpose of the window comparator is noise rejection to obtain a sharp cut-off band pass filter, between 300 and 3000 Hertz, for example. A pull-up resistor 77 is connected to a positive voltage source and feeds through a resistor 78 to a normally biased transistor 79, which gives a low true output on conductor 80, referring to negative logic, because of the pull-up resistor 81. If no voice signal is present on the input conductor 71, there is no signal on the output conductors 73 and 74, and the Op/Amps 75 and 76 are biased on by resistors 82, 83, and R33 to act as a current sink for the pull-up resistor 77, thus turning off transistor 79 and making the output conductor a high falso condition under negative logic. This is also true if some signal occurs which is less than 300 Hertz or higher than 3000 Hertz, so that it is assumed to be noise rather than voice, and hence the circuit is highly noise-rejecting. However, when a voice signal does appear on the input conductor 71, the window comparator 25 is biased off into a non-current sinking condition on both comparators 75 and 76, the pull-up resistor 77 thus turning on transistor 79 for a low true condition on output conductor 80. The level indicator lamp 41 is connected for energization through a transistor 79A, which is essentially in parallel with transistor 79, to be illuminated when there is a voice signal present.

The circuit of FIG. 5 is duplicated, one for the microphone 21 and one for the inductive pickup 21A. As stated above, when the local person is speaking into the mouthpiece 63, that voice signal is picked up both by the microphone 21 on the display panel 33 and by the inductive pickup 21A; thus, on the output conductor 80 for each of the two circuits, there will be a signal. However, when the distant voice is speaking, only the inductive pickup 21A will receive a signal and will provide an output on only that output conductor 80 of the inductive pickup 21A. Thus, the present neuromotor response apparatus 20 is one which conditions the microprocessor 29 to determine whether this is a local or distant voice, as per Table 1 which follows.

TABLE I

| Test Subject | μP Decode | Dialogue Local | Dialogue Distant | Monologue Local |
|---|---|---|---|---|
| Talking | Local | A · $\bar{B}$ | $\bar{A}$ · $\bar{B}$ | $\bar{A}$ · $\bar{B}$ |
| Listening | Distant | $\underline{A}$ · $\bar{B}$ | $\underline{A}$ · $\bar{B}$ | NV |
| Noise | Noise rejection | $\bar{A}$ · B | $\bar{A}$ · B | NV |
| Pause | Pause | A · B | A · B | A · B |

In Table 1 a truth table is set forth for each of dialogue local, dialogue distant, and monologue local. In this truth table, the letters "A" and "B" have been used, since each microprocessor 29 and 29A has been programmed identically, and the two inputs on $T_0$ and $T_1$ represent two different persons—the local and distant voice, respectively—for the microprocessor 29, and because of the exclusive OR gate 27, they represent the distant and local voices, respectively, for the microprocessor 29A. The microprocessor performs the decoding of the truth table, as set forth in Table 1. For example, under the dialogue, local voice, the truth table sets forth $\bar{A}.\bar{B}$. Because this is negative logic, the low true signal of each of these input signals on the terminals $T_0$ and $T_1$ indicates that the local voice is talking. The next item in this column indicates that the local voice is listening, which is the case whenever the distant voice is speaking. The third item in this column is some spurious signal or noise, and hence the microprocessor rejects this condition. The fourth item in the column is the only thing that is recorded as a pause, and this is when both A and B are high false, using negative logic, indicating an absence of signal on both input terminals $T_0$ and $T_1$. The truth table for the distant voice during a dialogue has the same two conditions as the local voice during a dialogue for the last two items in the two columns, yet it will be noted that the A signal is reversed for the first two items in the distant column relative to the local column. By this means, a single program may be used for the two microprocessors 29 and 29A.

Figure 6:
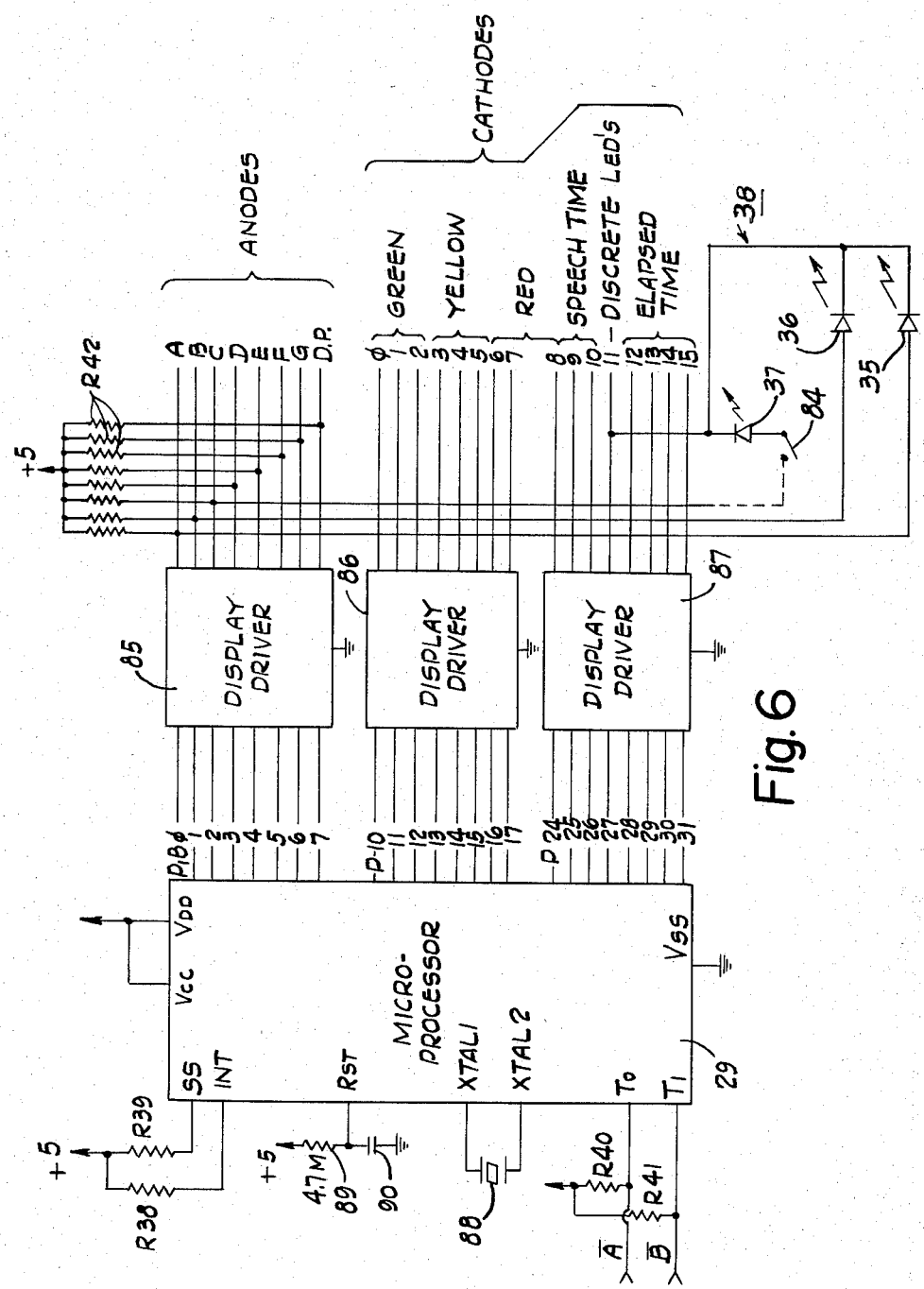
FIG. 6 is a schematic diagram of the microprocessor and display portion of FIG. 1.

FIG. 6 illustrates schematically the microprocessor 29, or also microprocessor 29A, together with a series of display drivers 85, 86, and 87 to drive the display unit 30, shown in FIG. 6 only as anodes and cathodes, of the various seven segment displays 45, 46, and 47 shown in FIG. 2. The microprocessor has the usual power supply and ground connections and the inputs A B are supplied to the terminals $T_0$ and $T_1$. Also a crystal 88 is connected to the crystal terminals to supply a clock or timer frequency. A resistor 89 and capacitor 90 are connected to a reset terminal RST to provide a slight time delay of powering up this reset terminal to make certain that everything is reset to zero on initial power-up by turning on the main ON/OFF switch 44 on the display panel 33 of FIG. 2.

FIGS. 9-16, cumulatively, show the flow chart indicating the operation of the microprocessor 29. On this flow chart, a number of instructions are abbreviated, in accordance with Table 2, in order to save space on the flow chart.

TABLE 2

| | |
|---|---|
| AFTH | "A" Floor time (in tenths of seconds) |
| ASTATE | Status of "A" (0 = listening; 1 = talking; 2 = pausing) |
| CODE | One minute window status (0 = green; 1 = yellow; 2 = red; 3 = before 1 minute) |
| CPAUSE | Current pause length (in tenths of seconds) |
| PNUM | Number of pauses in one minute window |
| GPAUSE | Number of pauses that occurred during a green |

TABLE 2-continued

| | |
|---|---|
| | code |
| YPAUSE | Number of pauses that occurred during a yellow code |
| RPAUSE | Number of pauses that occurred during a red code |
| SAVEA | Data memory location used to store accumulator when interrupt routine is entered |
| SECS | Integer number of seconds in TIME (0 to 59) |
| TCOUNT | Value loaded into timer so that exactly 0.1 second passes between executions of Loop. |
| TINTS | Number of timer interrupts before 0.1 second interval |
| TCPTG | Total cumulative pause time during green code |
| TCPTY | Total cumulative pause time during yellow code |
| TCPTR | Total cumulative pause time during red code |
| TEMP | Temporary storage |
| TENTHS | Number of tenths of a second in TIME (0 to 9) |
| TIME | Interview time clock (in tenths of seconds) |
| MAJOR CODE SECTIONS: | |
| TIMER | An interrupt routine that is executed every 0.1 second, and is invoked by the internal microcomputer timer. This routine does all of the time accounting during a monitoring session. |
| RESET | This section of code that is always running. It is an infinite loop that displays the time and results and monitors the RUN/STOP switch. |
| COMPUT | This subroutine is called at the end of a monitoring session. It computes the three average pause durations, the percent floor time, and the LED color (number of pauses per minute). |
| TIMDIS | This subroutine converts TIME to minutes and seconds, and displays it on the seven segment displays. This is called both during and after a monitoring session. |

Figure 9:
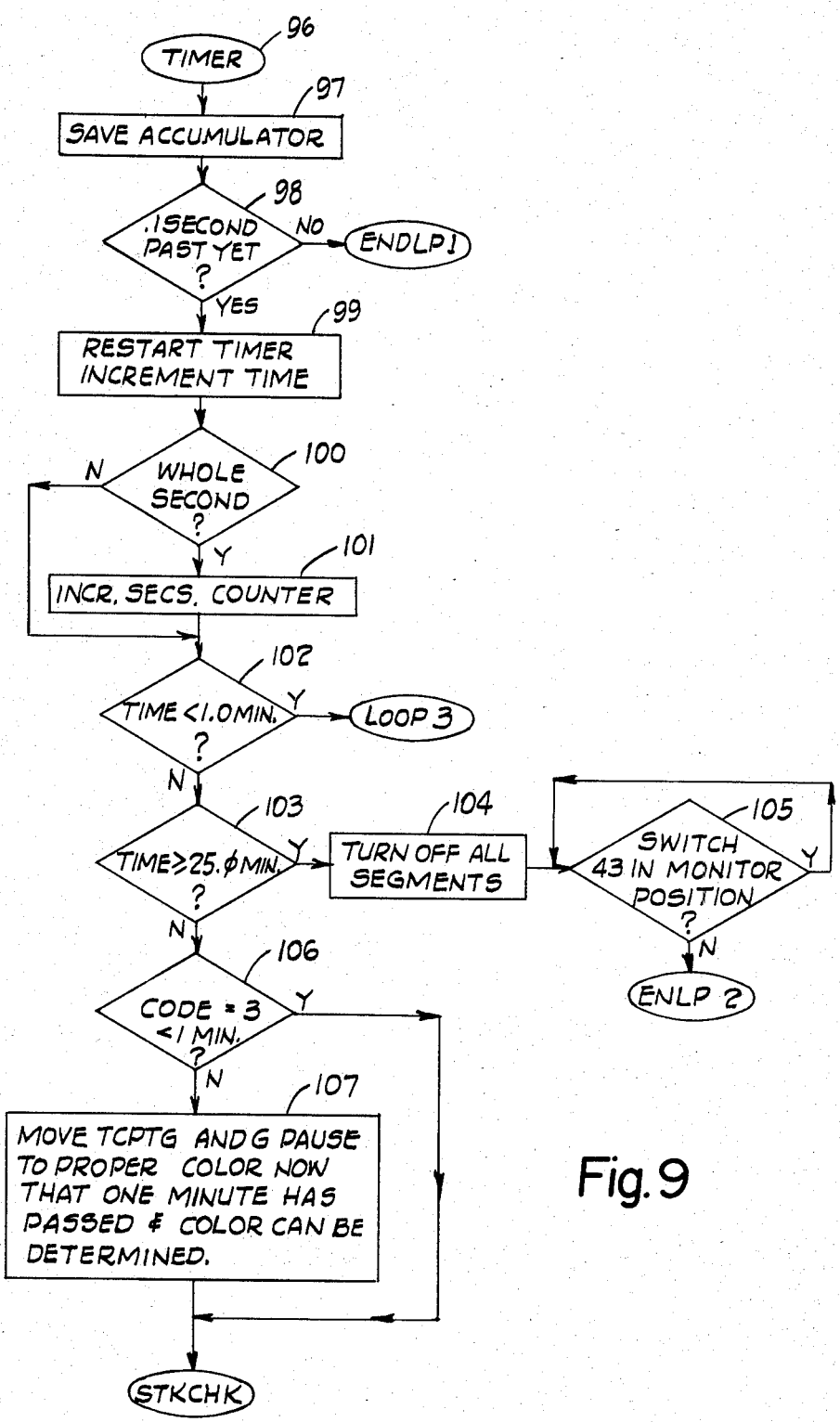
FIGS. 9–16 are figures illustrating a flow chart of operation of the software controlling a microprocessor.
Figure 10:
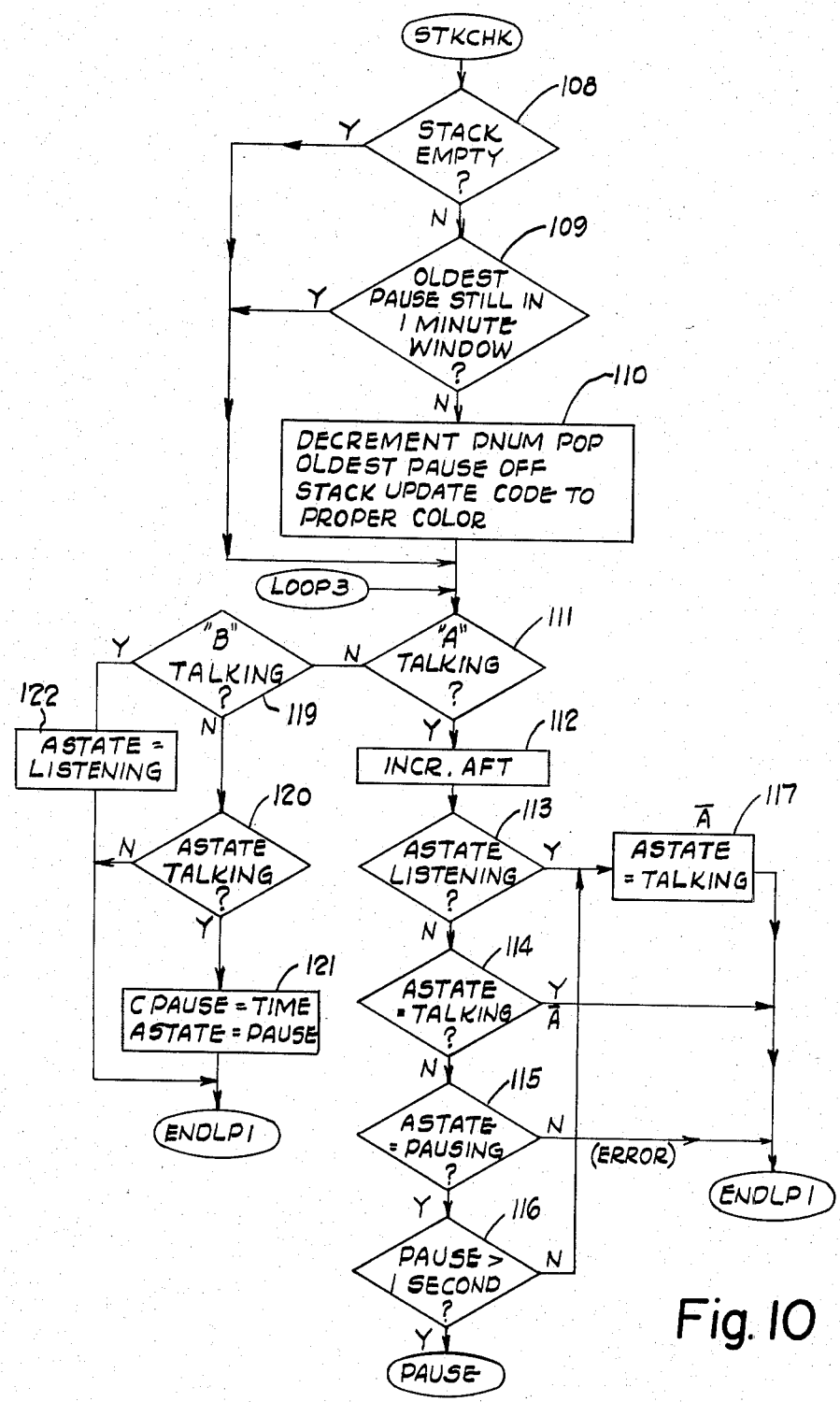
Figure 11:
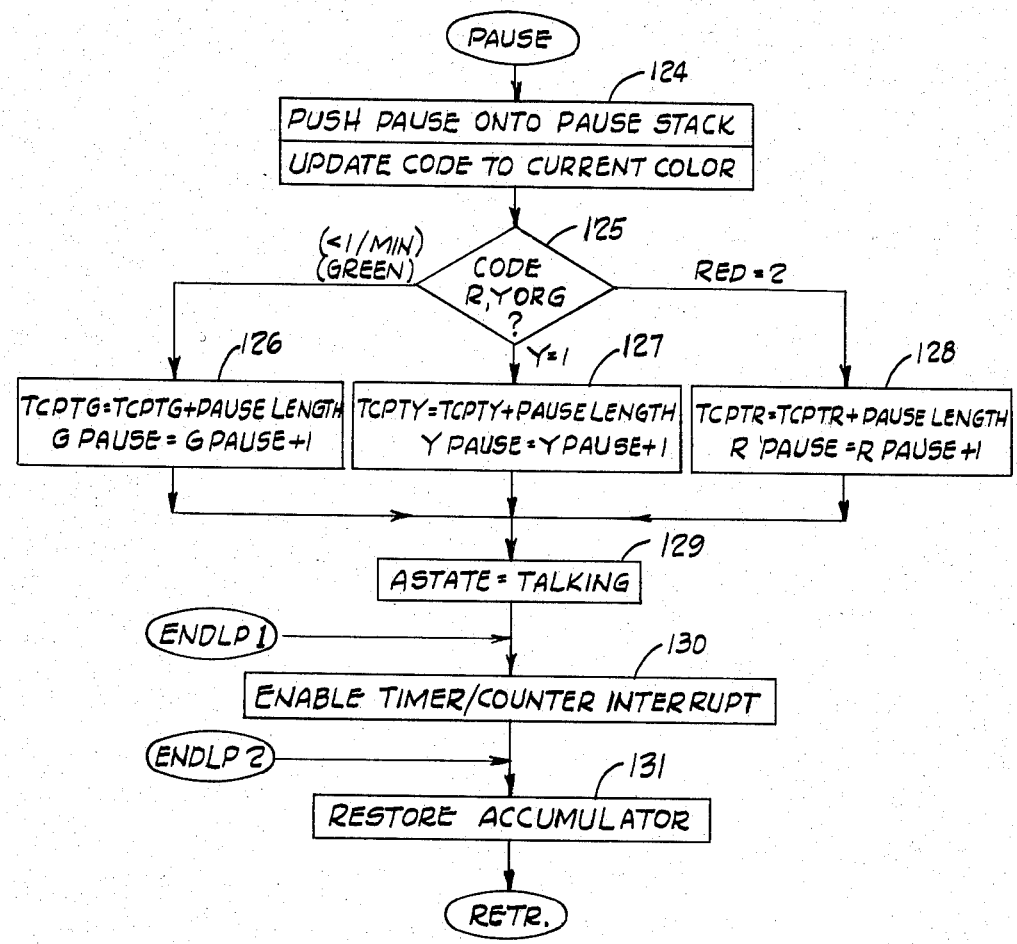

In general, FIGS. 9, 10, and 11 are that part of the flow chart which shows the data collecting portion, and FIGS. 12–16 are that part of the flow chart which shows the data display. FIGS. 9, 10, and 11 refer to a timing function which may be considered all part of a timing decision block 95 on FIG. 12. In FIG. 9 a timer is indicated at 96, which is controlled from the crystal oscillator 88 connected to the microprocessor 29. This timer operates at a rate higher than 0.1 second, but the timing sequence of FIGS. 9, 10, and 11 operates at a rate of ten times per second. The statement block 97 in FIG. 9 indicates that the count in the accumulator is saved or kept the same. Decision block 98 asks whether 0.1 second has yet passed. If the answer is "No," then the flow chart proceeds to the end of loop 1, discussed below. If the answer is affirmative, then statement block 99 states that the timer is restarted and the time is incremented. Decision block 100 inquires whether a whole second has passed, and if the answer is in the affirmative, then statement block 101 indicates that the counter which counts seconds is incremented. If the answer is in the negative, then this seconds counter is bypassed. The decision block 102 asks the question whether the time is less than 1 minute, and if the answer is affirmative, then one proceeds to loop 3, discussed below; and if the answer is negative, then decision block 103 questions whether the time is equal to or greater than 25 minutes. If the answer is affirmative, then statement block 104 indicates that all segments are turned off because, for this particular embodiment, this was the maximum memory capacity available. Decision block 105 asks whether the run/stop switch 43 is in the monitor position, and if the answer is affirmative, then the program keeps looping through this block 105 until the answer is negative, whereat the flow proceeds to end loop 2 shown on FIG. 11.

After the decision block 103 on FIG. 9, if the answer is negative, then decision block 106 asks whether the one minute window status has passed. Table 2 shows that the green code or mode is zero, the yellow code is 1, and the red code is 2, and before 1 minute has expired, the code is 3. If the answer is negative, this means one minute has passed, and therefore statement block 107 shows that the total cumulative pause time during the green code, and also the green pause, are moved to the proper color now that one minute has passed, and the color can be determined. If the answer to block 106 is in the affirmative, this decision block 107 is bypassed and one proceeds directly to FIG. 10.

On FIG. 10, decision block 108 inquires whether the stack or counter is empty. This is a downcounter, counting down towards zero. If the answer is negative, decision block 109 inquires whether the oldest pause is still in the one minute window, and if the answer is negative, then statement block 110 states that the number of pauses in the one minute window is decremented. Also, the oldest pause is taken off the stack and the code is updated to the proper color. On either decision block 108 or 109, if the answer is affirmative, then this statement block 110 is bypassed.

The lower portion of FIG. 10 is essentially that part of the flow chart which explains how the four different conditions of the truth table (Table 1) are interrogated. Decision block 111 asks whether A is talking, and this is the person being monitored or the subject, whereas person B is generally considered the interviewer, such as a doctor. If the answer is affirmative, this is signified by A, which is negative logic, indicating a logic true condition for A talking. Statement block 112 indicates that if the answer is affirmative, then A's floor time or speech time is incremented, and decision block 113 asks the status of the A register, as to whether it previously had been changed to indicate that A was listening. If true, then block 117 states it is changed to indicate that A is now talking, and the flow loops back to the end of loop 1. If the answer to 113 is negative, decision block 114 asks the status of the A register, as to whether it previously had been changed to indicate that A was talking. If affirmative, then the flow loops back to the end of the loop 1. If the answer to 114 is negative, then decision block 115 asks the status of A, as to whether he is pausing. If the answer is affirmative, then decision block 116 asks whether the pause is greater than one second, and if the answer is in the affirmative, then this is a true hesitation pause according to one embodiment of the invention because this pause of A exceeds a preselected time interval. To return to decision block 114, if the answer is affirmative, then one also proceeds to the end of loop 1. If the answer to decision block 115 is negative, then this is an error, shown in truth table 1 as caused by noise, for example. If the answer to decision block 116 is negative, then one proceeds back to the statement block 117 because such pause is too short to be a true hesitation pause.

The middle of FIG. 10 shows that decision block 111 asks whether A is talking, and if the answer is negative, decision block 119 asks whether B is talking. If the answer is negative, then decision block 120 inquires whether the status of the A register is that he is talking, and if the answer is in the affirmative, then statement block 121 indicates the time of the current pause length in tenths of a second. Also, the status of the A register is changed to show that A is pausing, and then one passes to the end of loop 1. If the answer to decision block 119 is affirmative, then statement block 122 indicates that the status of the A register is changed to show A is listening and one passes to the end of loop 1. If the decision block 120 answer is negative, then one passes to the end of loop 1.

After it has been determined in decision block 116 that the pause is more than the predetermined time period (in this example, one second), then one passes to that portion of the flow chart on FIG. 11. This decision of a pause is passed to the statement block 124, which shows that the hesitation pause is pushed onto the pause stack or memory and the red, yellow, or green code is updated to the current color. The decision block 125 asks the question whether the code is red, yellow, or green. If it is less than one pause per minute, namely zero pauses in the last minute, then the code is green; if there was already one pause in the preceding minute, then the code is yellow; and if there were two pauses in the preceding minute, the code is red. The green code leads to statement block 126, wherein the pause length is added to the total cumulative pause time during the green code, and the green pause counter is incremented by one count. If the code is yellow, the statement block 127 shows that the length of that yellow pause is added to the total cumulative pause time during the yellow code, and the yellow pause counter is incremented by one count. If the code is red, the statement block 128 shows that the pause length is added to the total cumulative pause time during the red code and the red pause counter is incremented by one unit. All three of these statement blocks then pass to statement block 129, which changes the status of the A register to indicate that A is talking. This necessarily is the case by the definition that a hesitation pause is a pause bounded by the speech of the subject A. After this statement block 129 end of loop 1 re-enters the flow chart, and statement block 130 shows that the timer/counter interrupt is enabled. After this end loop 2 enters the flow chart, and then statement block 131 shows that the accumulator is restored, the program returns from the interruption which started that entire timer subroutine of FIGS. 9, 10, and 11. This timer subroutine occurs in less than one-tenth of a second, and then repeats every one-tenth of a second.

Figure 12:
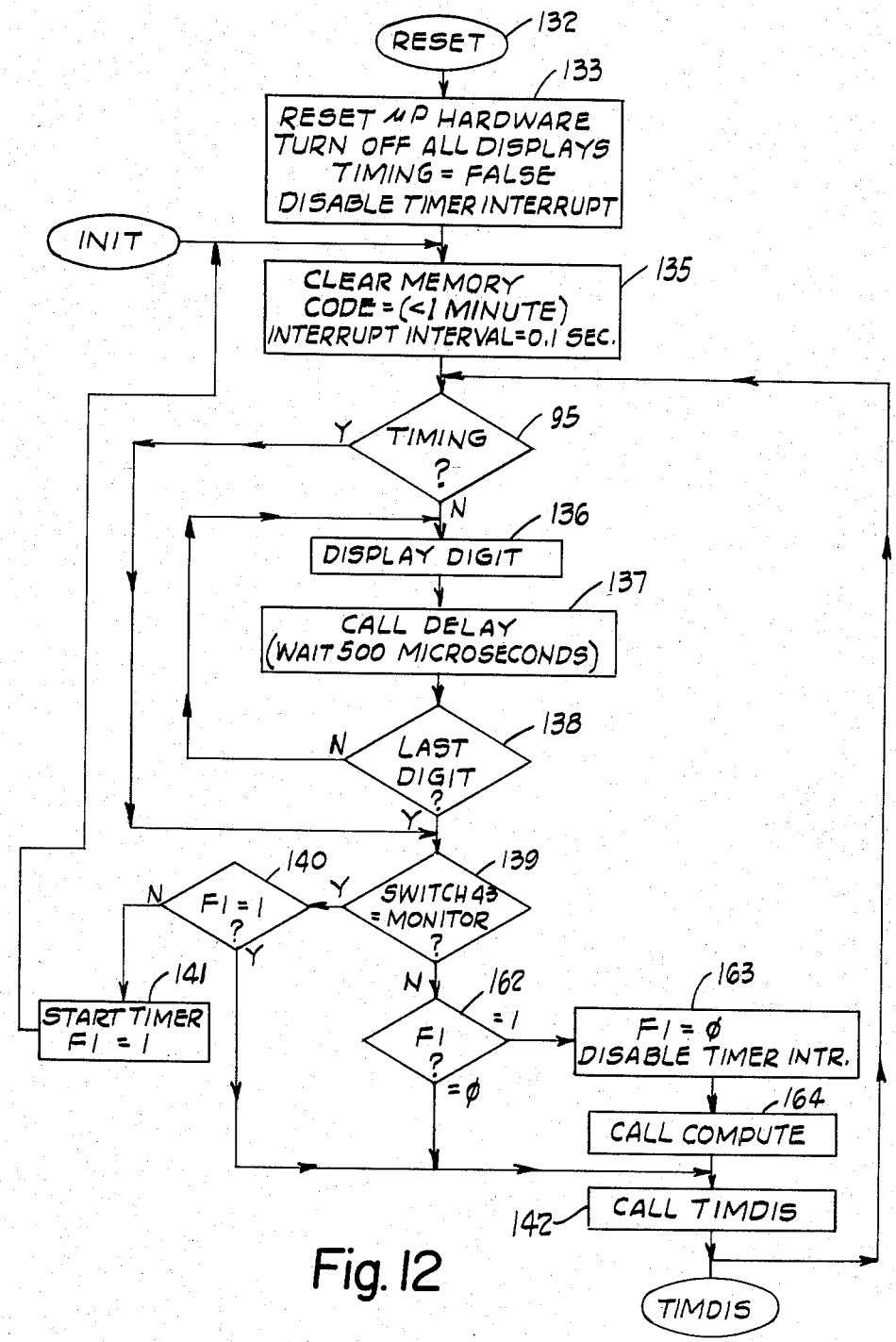
Figure 14:
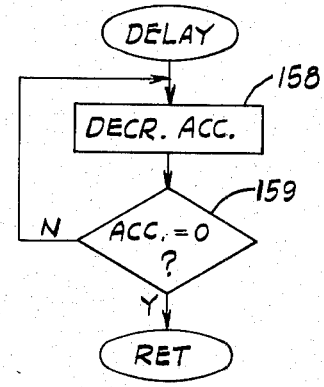

FIG. 12 may be considered the start of the main routine, wherein the ellipse 132 shows a reset and statement block 133 shows that this reset is of all of the hardware of the microprocessor which turns off all displays, the timing is equal to a false logic condition, and the timer interrupt is disabled. At this point, the program may be initiated, and the statement block 135 shows that the memory is cleared, the code equals less that one minute, namely the green code, and the interrupt interval is 0.1 second. From here, the flow chart passes to the timing subroutine 95, which has been previously explained in connection with FIGS. 9, 10, and 11. This timing subroutine is repeated ten times per second in order to interrogate the microprocessor terminals $T_0$ and $T_1$, and to process the information according to the truth table of Table 1. This timing block 95 of FIG. 12 asks the question whether the timing is still continuing, and if it is not, statement block 136 indicates that a digit should be displayed. Before the digit is displayed, statement block 137 calls for a delay of 500 microseconds, and this is for interdigit blanking to prevent smearing in the display of digits which are changing. This delay subroutine is shown in FIG. 14, and is called for at numerous places, as shown below. Decision block 138 asks whether this is the last digit, and if it is not, then the flow loops back to display the next digit. When it is the last digit, the program flows to the decision block 139.

To return to the decision block 95, which asks the question whether the program is timing, if the answer is affirmative, then blocks 136, 137, and 138 are bypassed and the program flows directly to this decision block 139, which asks the question whether the switch 43 is in the monitor position. This switch will normally be in the monitor position during a dialogue, and only at the end of the dialogue will the person normally want to switch this switch to the display position to determine his hesitation pauses and percent of speech time. Assuming that this monitor switch is in the monitor position, the decision block answer is affirmative, and it passes to a status flag decision block 140, which asks whether the flag 1 register is a 1. At the very start, when everything is reset, this will be reset to zero, so the first time through the answer will be negative, and it passes to a statement block 141 which starts the timer and sets the flag 1 register to a 1, and the program goes back to the decision block 135. The next time through, from the decision block 139 to block 140, this flag 1 register will be a 1, so that the program passes to a call time display block 142.

Figure 13:
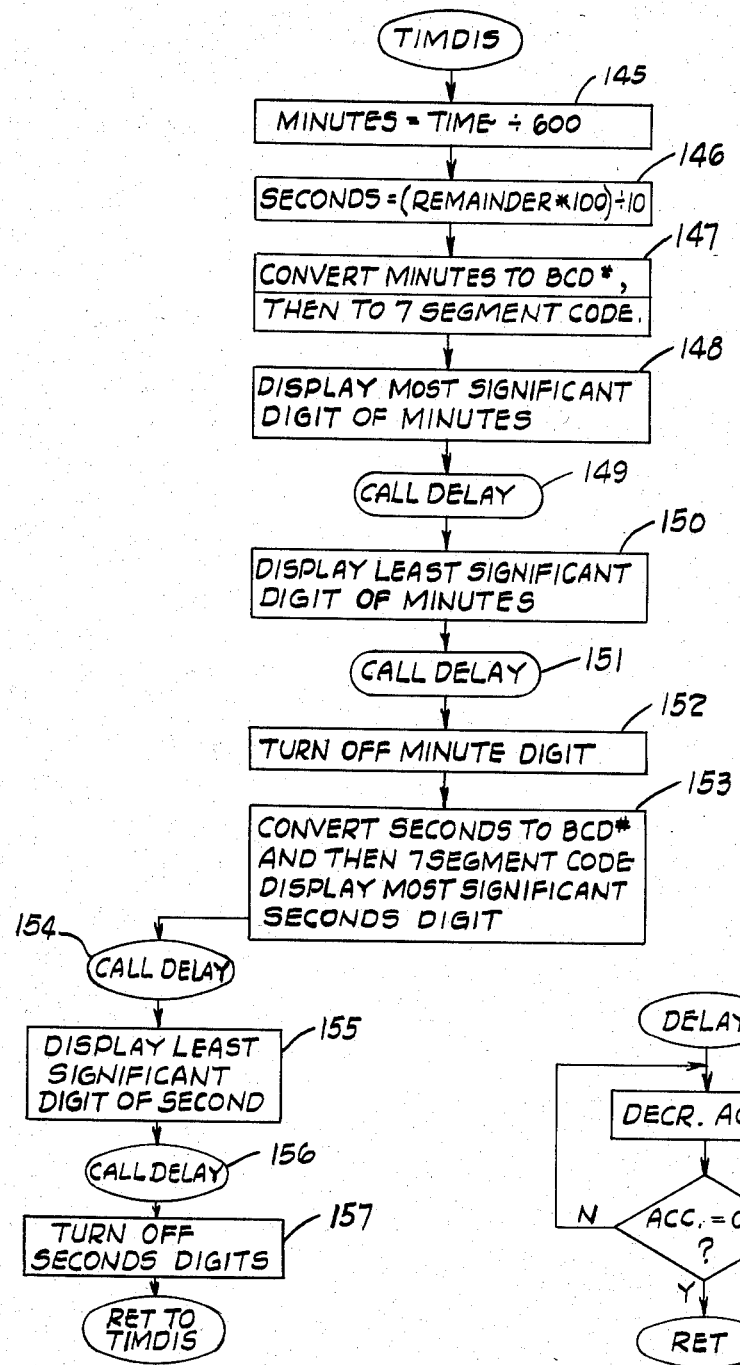

The time display program is set forth in FIG. 13, and is a separate subroutine to display only the elapsed time on the indicator 39 of FIG. 2. In this FIG. 13, the time display subroutine passes to a statement block 145, which determines the number of minutes by dividing the time by 600 because time is one-tenth of a second. Next, block 146 determines a second by having the remainder multiplied by 100 and divided by 10. The minutes are converted to binary coded decimal in block 147 and then converted to a seven-segment code. Block 148 states that the most significant digit of the minutes is displayed and then block 149 calls for the delay subroutine of FIG. 14 for interdigit blanking. Block 150 states that the least significant digit of minutes is displayed, and another delay subroutine is called for at 151. Block 152 turns off the minute digit because the time required for the following long computation would mean that the duty cycle on the least significant digit would be longer than that on the most significant digit, and hence would appear brighter. Block 153 converts the seconds to binary coded decimal and then to seven-segment code with a display of the most significant seconds digit. Again, the delay subroutine is called at 154, and block 155 states that the least significant digit of the seconds is displayed, with delay again called for at 156, and the statement block 157 states that the seconds digits are turned off and then there is a return to the time display. Therefore, the elapsed time is continually updated and displayed.

The delay subroutine of FIG. 14 may be anything suitable to obtain a small delay of 500 microseconds, for example, and when the delay subroutine starts, it passes to a statement block 158, which states that an accumulator is decremented, namely a downcounter which has been preloaded to have a given preset number therein. The program passes to a decision block 159, which asks whether the accumulator has decremented to zero. If the answer is negative, it loops back to decrement the accumulator once again. When the accumulator has decremented to zero, the delay has been accomplished and the delay subroutine returns to its starting point.

To return to FIG. 12, at the end of the conversation if the subject wishes to learn how well he performed, he will move the switch 43 from the monitor to the display position. At this point, decision block 139 will note that the monitor switch is no longer in the monitor position, and thus the program will pass to decision block 162. If the program has not yet really started, this flag 1 register may be in the zero condition, which will call only for time display in the statement block 142. However, if a dialogue has been monitored and the flag 1 register has been changed to a 1 condition, then the decision block 162 will pass the program to a statement block 163, which sets the flag 1 register back to a zero position and disables the timer interrupt.

Next statement block 164 calls for the compute subroutine, and also calls for the time display, which is a continuous display of the elapsed time.

Figure 15:
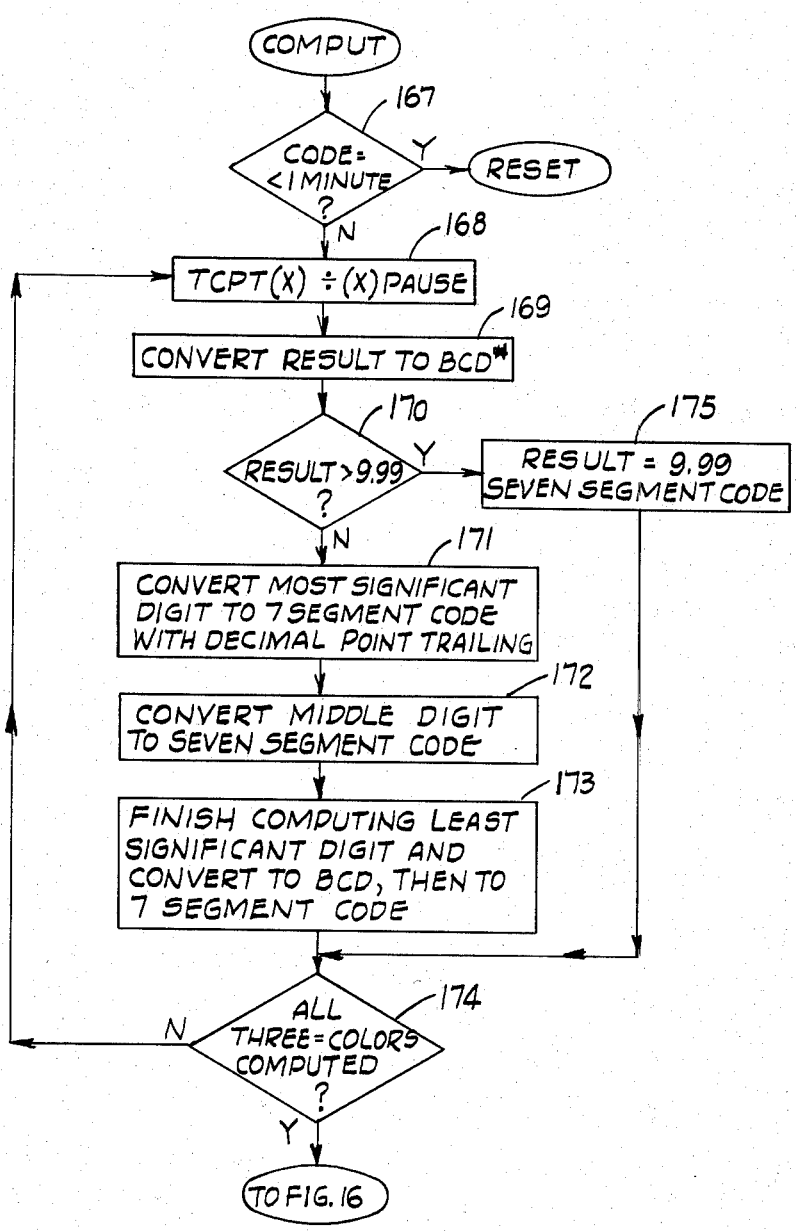
Figure 16:
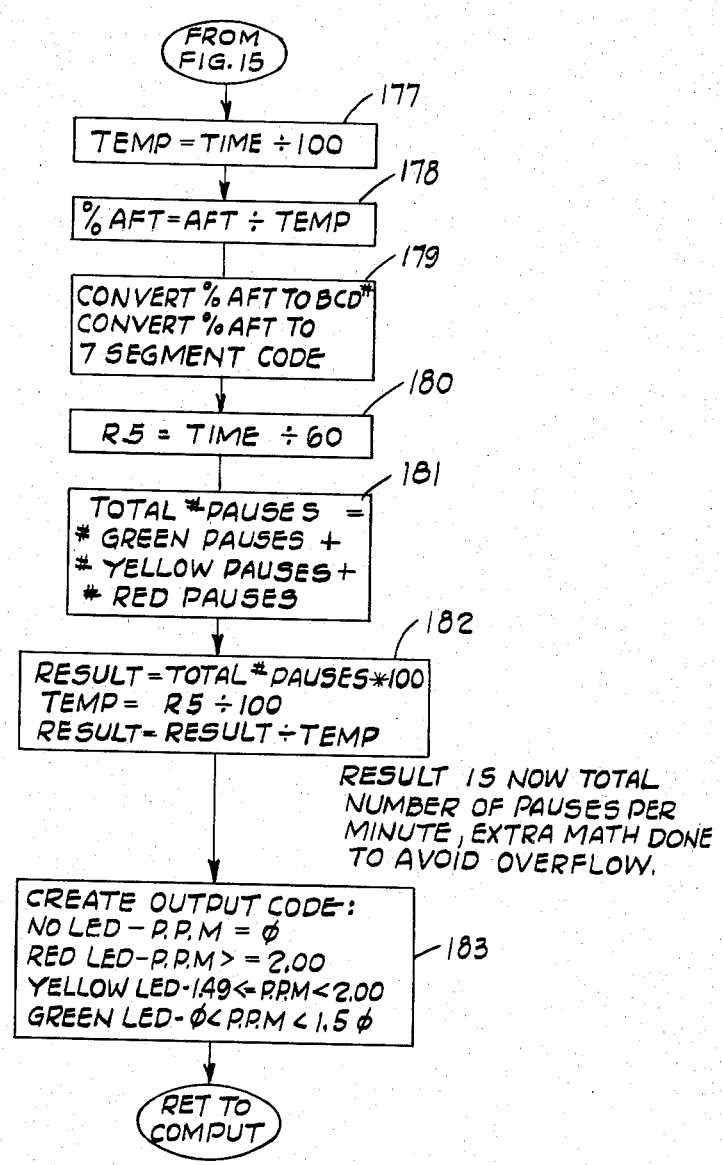

FIGS. 15 and 16 give the compute subroutine as called for by block 164 on FIG. 12. At the top of FIG. 15, one notes that the compute subroutine passes to a decision block 167, which asks whether the code, namely the one-minute window status, is less than 1 minute. If the answer is in the affirmative, then the program goes back to reset, which is at the top of FIG. 12. If the answer is negative, the program passes to the statement block 168, wherein the total cumulative pause time for X is divided by the pause of X. By X is meant each of the three green, yellow, and red codes, respectively. Block 169 states that the result is converted to binary coded decimal. Decision block 170 asks whether the result is greater than 9.99, and if the answer is negative, then the most significant digit is converted to seven-segment code, with the decimal point trailing, and this is done in block 171. Block 172 states that the middle digit is converted to seven-segment code, and block 173 states that the least significant digit is computed and converted to BCD, and then to seven-segment code. The result passes to decision block 174. To return to decision block 170, if the answer is in the affirmative, the program passes to statement block 175, which states that the result being 9.99, the maximum number capable of being displayed in this embodiment, it is converted to seven-segment code and passed to the decision block 174. This decision block asks whether all three colors have been computed, and if not then the program returns to the statement block 168. When all three colors have been computed, the program passes to the flow chart on FIG. 16, and to the statement block 177, whereat the temporary storage is equal to the time divided by 100.

Next, the statement block 178 states that the percent of A's floor time or speech time is determined, and it is determined by A's floor time divided by the number in the temporary storage. Block 179 states that the percent of A's floor time is converted to binary coded decimal, and then to seven-segment code. Block 180 states that the time divided by 60 is stored in a miscellaneous register 5, and block 181 states that the total number of pauses is equal to the number of green pauses plus the number of yellow pauses, plus the number of red pauses. Block 182 states that the result is equal to the total number of pauses times 100, and the temporary storage is equal to the number stored in miscellaneous register 5 divided by 100, with the new result equal to the old result divided by the temporary storage. This shows that the result is now the total number of pauses per minute, with the extra math done to avoid overflow of the register. Block 183 states that an output code is created. No indicator lamps 35, 36, or 37 are illuminated if the pauses per minute are equal to zero. The red LED lamp 37 is illuminated if the pauses per minute are greater than two. The yellow LED lamp 36 is illuminated if the pauses per minute are between 1.49 and 2 per minute. The green LED lamp 35 is illuminated if the pauses per minute are between zero and 1.50 (which is in the order of one pause per minute). Thus the dominant or average frequency level of the hesitation pauses is indicated by the illumination of the respective lamp 35–37. Hereafter, the program returns from where it was called, namely, the beginning of the compute subroutine.

In summary, it will be noted that FIG. 12 sets forth generally the entire microprocessor program, starting with the reset of all hardware and ending with calling for a time display of the elapsed time, and then when the switch 43 has been changed from monitor to display, the program calls also for a computation of the pauses, and hence a display of such pauses, for each of the red, yellow, and green codes, together with percent of speech time of each of the two persons participating in the dialogue.

Figure 8:
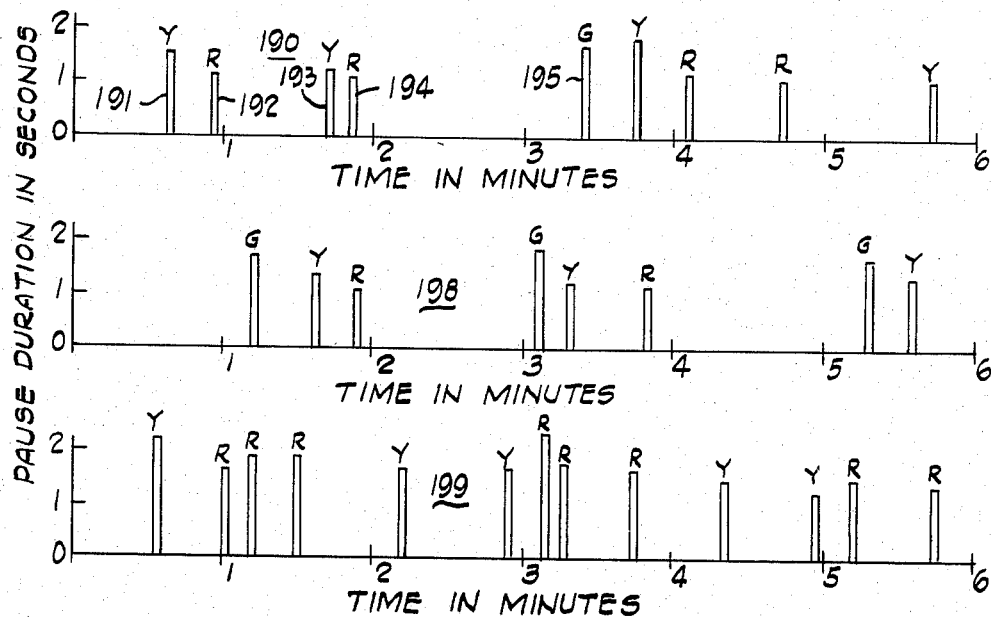
FIG. 8 is a graph of representative pause durations relative to time.

FIG. 8 shows several graphs of pause durations plotted against the time of the dialogue. Graph 190 shows a graph of the hesitation pauses of the subject A as displayed for the local voice of FIG. 2. In this particular example, the hesitation pause is defined as an absence of vocal sounds uttered by the subject, bounded by the speech of the subject, and having a duration of one second or more. Therefore, all of the pauses in Graph 190 have a pause duration of one second or more. Each of the pauses has a letter G, Y, or R above it to indicate whether it is a green, yellow, or red code pause. The first pause 191 is a yellow code pause, because it has occurred at less than one minute of time of the dialogue with the distant voice, such as a doctor or interviewer, and therefore the pause rate is greater than one per minute. The next pause 192 is a red code pause because it has occurred at less than one minute of the dialogue, and hence the rate is greater than two pauses per minute. The third pause 193 is assigned a yellow code because in the preceding one minute there was only one other pause, namely pause 192. The fourth pause 194 is assigned a red code because in the preceding one minute there were two other pauses. The next pause 195 is assigned a green code because in the preceding one minute there were no other pauses. The remaining pauses in this Graph 190 are assigned a code by the same criteria. The result is shown for the local voice in FIG. 2, namely, the average pause duration for the green code pauses (in this case only a single pause) was 1.70. The average pause duration for the yellow code pauses was 1.38 and the yellow indicator lamp 36 would be illuminated because there was a total of nine pauses in slightly less than a six-minute dialogue; thus, this is at a rate greater than 1.5 pauses per minute and less than two pauses per minute. The average duration of the red code pauses was 1.09, again as displayed for the local voice on FIG. 2. A red light in the local voice and a green light in the distant voice indicates a discrepancy of 0.59 seconds or a failure of harmony based on dominant mode duration alone. In addition, the greater dysrhythmia of the local voice further adds to a discordance. Significantly shorter pauses by the local voice suggest speech may be too rapid, in addition to being dissonant, for the distant voice to assimilate what is being said. This would be even more likely if the distant voice were more poorly adapted with dysrhythmic speech, e.g., red mode at 1.68 seconds.

Graph 198 in FIG. 8 displays the distant voice pauses in duration and at time locations during the dialogue with the subject A. In Graph 198, there are eight pauses, which have been assigned a green, yellow, or red code in the same manner as those assigned for Graph 190. The average pause duration of the three green code pauses is 1.68, and the green indicator lamp 35A would be illuminated because there are only eight pauses during the approximately six-minute dialogue; hence, this is at a pause rate of less than 1.49 pauses per minute. The average duration of the yellow code pauses is 1.41 and the average duration of the red code pauses is 1.12. This is as displayed on the distant voice section of FIG. 2. Also, FIG. 2 shows that the subject A utilized 67% of the total speech time, and the distant voice B utilized 30% of the speech time. These two graphs illustrate that the distant voice had better prosody than the subject voice in having a greater number of green pauses and a fewer total number of pauses, so that the green indicator lamp 35A was illuminated, whereas, for the subject voice the yellow indicator lamp 36 was illuminated, indicating a greater number of pauses. The subject had a desirable increase of pause duration from red to yellow to green, as shown by the increased pause duration on the display panel 30. The interviewer also had the same desirable increase in pause duration from red to yellow to green, and further had greater prosody and the best correlation between the pause duration and pause rate because the green indicator lamp was illuminated, indicating a desirable low rate of pauses. Further, the interviewer attempted to maintain high fluency while matching the subject in his hesitation pause duration, thus establishing a good rapport with the subject and a reassuring dialogue. This can be quite important where the interviewer is a doctor speaking on the telephone to a subject who might be under severe depression or have suicidal tendencies.

Graph 199 of FIG. 8 is a graph of the hesitation pauses in a dialogue of a subject who is more hesitant than the subject of Graph 190. Again, the various pauses have been assigned a red or yellow code, and since there was no minute during the dialogue when there was not at least one hesitation pause, none of the succeeding pauses was assigned a green code. Therefore, in the display of the green, yellow, and red pause durations on the display panel, there would not be any digital display of pause duration for the green code pauses. The yellow code pauses would average about 1.66 and the red code pauses would average about 1.76 seconds in duration. Also, the red indicator lamp 37 would be illuminated because a total of 13 pauses in the less than six minutes of dialogue would be a pause rate greater than two pauses per minute.

When a subject views the display panel of FIG. 2 and notes that his red code light 37 or 37A is illuminated, the display panel has the green level lights 41 and 41A illuminated, as is usually the case, and also the other person's green indicator lamp 35 or 35A is illuminated. He will observe his red light framed by green lights. This framing of red by green light enhances a person's perception of his own red light, and hence awareness of his being in a red or unsatisfactory code. The opponent cells in the visual cortex are the physiological basis for this light-framing configuration.

Figure 7:
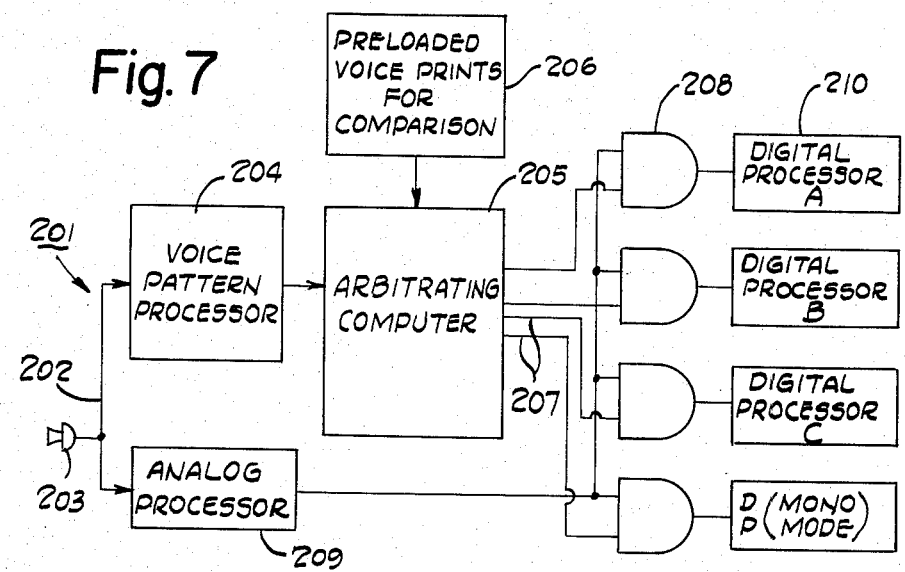
FIG. 7 is a block diagram of a modification utilizing a voice print comparator.

FIG. 7 illustrates a modification wherein a neuromotor response apparatus 201 of a modified form is shown. In this case, more than two persons may utilize the apparatus. An audio input is supplied on line 202 from a suitable source such as an omnidirectional microphone 203, and which would be used in a classroom, for example, having an instructor and several students. The line 202 conducts the audio signal to a voice pattern processor 204, whereat the voice of that particular person speaking is processed, e.g., digitally, and directed to an arbitrating computer 205 whereat it is compared with the preloaded voice prints from a memory unit 206. such memory unit preloaded voice prints would have been pre-established in order to provide in the computer 205 a means to identify the person speaking. The output would then appear on the selected one of a plurality of output lines 207 to one input of a plurality of AND gates 208. The other input of these AND gates 208 would be each connected to the output of an analog processor 209 which would be the circuits of FIGS. 3 and 5 in sequence, for example. Thus, the particular selected output line 207 would enable that particular AND gate and the signal would be passed to the respective one of a plurality of digital processors 210, such processor being that of FIG. 6, for example. In this way, there could be a determination and display of the pause duration and pause rate for each person in a large group.

FIG. 17 is a modification showing a neuromotor response apparatus 215, in this case responsive to the pedal action or foot response of a subject. The apparatus 215 is an intrapersonal response apparatus responsive to only a single person but with the possibility of a dual, triple, quadruple determination and display of the response of the hands and the left foot and right foot of such person. The apparatus 215 is adapted to be used with a motor vehicle or vehicle simulator having a steering wheel, an accelerator 216 and a brake pedal 217. It is therefore suitable for a vehicle with either an automatic or manual shift transmission. In the latter case, the vehicle or simulator will also have a clutch pedal 218. The accelerator pedal 216 is linked to the movable element of a potentiometer 219, and passed through a differentiator consisting of a capacitor 220 and resistor 221, so that a slight change in the accelerator pedal setting produces a sharp spike which adds or subtracts from an average bias level of about six volts. This is amplified in a transistor 222, and then passed to a pair of differentiators. The first differentiator includes a capacitor 223 and resistor 224, then to a buffer gate 225 and then to an OR gate 226. The second output of transistor 222 passes to a differentiator which includes capacitor 227 and resistor 228 with a signal passed to an inverter gate 229 and thence to the OR gate 226. The spike on the input of the transistor 222 is amplified to become a pulsatile wave, either positive or negative on the output thereof. The buffer gate 225 is biased just below the threshold by means of a resistor 230 and the resistor 224, and hence passes only the positive going pulsatile wave signals to the OR gate 226. The inverter gate 229 is biased just above the threshold by a resistor 231 and the resistor 228 so that it passes only the negative going pulsatile wave signals to the OR gate 226. The inverter gate 229, of course, inverts the signals so that they are positive going, the same as the signals coming from buffer gate 225. Thus, on the output line 232, accelerator signals will be present, giving a positive logic true signal for any slight movement of the accelerator toward either increased or decreased speed.

The brake pedal 217 may actuate a separate electrical momentary closed switch, but for convenience may operate from the brake light switch 233 to actuate a brake light 234. An optional resistor 235 may be connected to ground in parallel with the brake light in case this brake light filament burns out. The signal from the brake light switch 233 passes through two inverter gates 236 and 237 to obtain double inversion for buffering and level shifting. The signal of actuation or deactuation of the brake pedal 217 thus appears on the output line 238, and this may be considered the B signal input to the microprocessor on the circuit of FIG. 6. The signal from the accelerator output line 232 may be considered the A signal, again to such microprocessor of FIG. 6. These two signals on lines 232 and 238 are connected on inputs to an OR gate 239, and the output thereof supplies an interrupt signal to alert the microprocessor.

Where the apparatus 215 is to be usable with a vehicle with a manual shift transmission, having the clutch pedal 218, a clutch actuation signal is provided. The clutch pedal is connected to actuate a momentary close switch 242 as the clutch disengages. The signal from switch 242 passes through two inverter gates 243 and 244 and appears on output line 245. This line output may be considered a C signal, again to a microprocessor of FIG. 6. That line is also connected to an input of the OR gate 239 for an interrupt signal. OR gates 246, 247, and 248 are connected across the pairs of output lines 232,238; 238,245; and 232,245 to provide additional inputs to microprocessors of FIG. 6 of A or B; B or C; and A or C. The accelerator response microprocessor, such as the one in FIG. 6, would have the input at $T_0$ from the accelerator signal A, and the input at $T_1$ from the B+C signal from OR gate 247. The brake response microprocessor would have the $T_0$ and $T_1$ inputs from the brake signal B and the A+C OR gate 248, respectively. The clutch response microprocessor would have the $T_0$ and $T_1$ inputs from the clutch signal C and the A+B OR gate 246, respectively.

FIG. 18 shows a flow chart 250 of the operation of the neuromotor response apparatus 215 of FIG. 17. Block 251 indicates that upon the first interrupt from the OR gate 239, it is passed to block 252, which states that the event which caused the interrupt is stored. i.e., either the A, B or the C event. Block 253 indicates that the timer is started and decision block 254 asks the question whether there has been an interrupt. If the answer is negative, then block 255 shows that the program continues. If the answer is in the affirmative, block 256 shows that there is a summation of the time of the interrupt together with the time already on the trip timer. Decision block 257 asks the question whether that latest interrupt is by the same input, A, B, or C, as the previously stored event per statement block 244. If the answer is negative, block 258 states that the timer is cleared and the flow returns to block 252. If the answer is affirmative, then statement block 259 states that the proper event counter is incremented, and block 260 states that the time for that particular event is summed with the proper time register. The program then flows back to clear the timer and repeat starting at block 252.

This program preferably would not display the information while the motorist was driving or being tested on a vehicle simulator, but would display it only upon turning off the ignition switch, thus avoiding distracting the driver during the trip or test. Display of the information could be on a display panel such as panel 33 in FIG. 2. The accelerator actuations, either positive or negative, would be displayed on the local display panel 30 and the brake actuations would be displayed on the distant panel 30A. A third display panel, similar to the other two, would display the clutch actuations. A fourth display panel could display the steering wheel events. Five registers would be used for the dual display and at the trip termination, these registers would yield data as follows: (1) the total trip time; (2) accelerator-to-accelerator events; (3) brake-to-brake events; (4) accelerator-to-accelerator total time; and (5) brake-to-brake total time. Where the triple display was utilized, additional registers would yield data on: (6) clutch-to-clutch events; (7) accelerator-to-clutch events; (8) clutch-to-accelerator events; (9) brake-to-clutch events; and (10) clutch-to-brake events. In a quadruple display, additional registers would yield data on the accelerator, brake, and clutch interaction with the steering wheel. By extending these registers, time and events could be stored as those falling within a plurality of timed interruption rates for display in the three digital readouts 45, 46, and 47 on the display panel 33. Final computation would divide the event time by the event number, yielding the average time per event.

Figure 19:
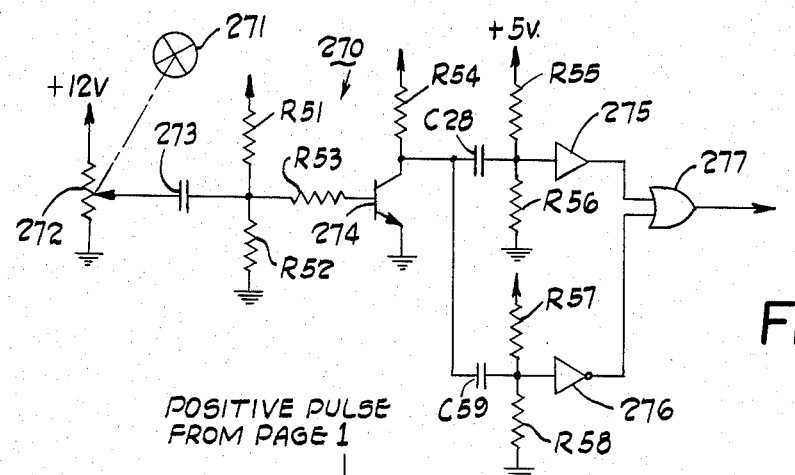
FIG. 19 is a schematic diagram of a modification determining steering wheel response in a motor vehicle.

FIG. 19 illustrates schematically the neuromotor response apparatus 270, wherein a steering wheel 271 is moved by a neuromotor response, namely, the movement of the hands of the vehicle operator. The steering wheel 271 is connected to the movable element of a potentiometer 272 in a circuit which is similar to the neuromotor response apparatus 215 of FIG. 17. The potentiometer is connected across the vehicle voltage source, such as 12 volts, so that as the steering wheel is moved, a signal is passed through a capacitor 273 and amplified by transistor 274 as either a positive going or negative going pulse, which is passed by a buffer gate 275 or an inverting gate 276, respectively, to an OR gate 277. Thus, movement to the right or left of the steering wheel 271 produces a pulse output from the OR gate 277. This signal is passed to the microprocessor, and the flow chart of FIG. 20 illustrates the operation of the microprocessor similar to that shown in FIG. 6.

Figure 20:
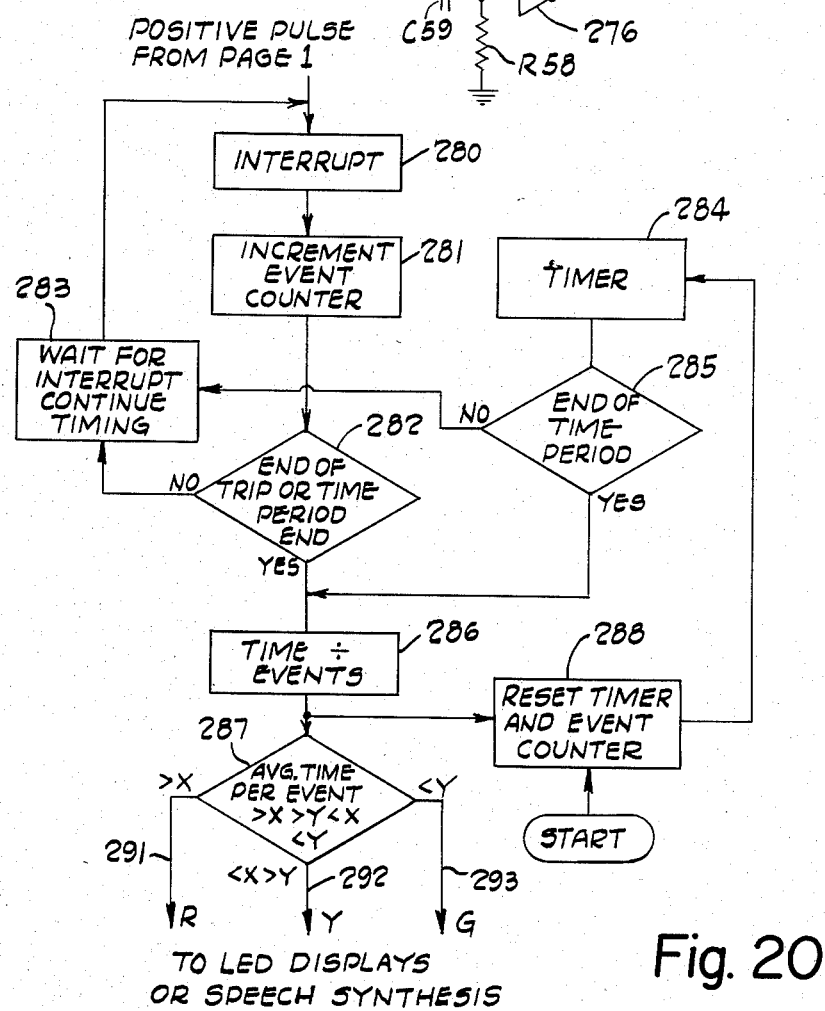
FIG. 20 is a flow chart of operation of the software controlling a microprocessor.

FIG. 20 is a flow chart illustrating that the pulse is supplied to a statement block 280 as an interrupt signal, and statement block 281 indicates that the first thing that occurs is that the event counter is incremented to the next higher numeral. The decision block 282 asks whether this is the end of the trip or the end of the time period, and if the answer is negative, then statement block 283 states that the signal flow waits for the next interrupt. At the same time, the timer 284 emits a periodic clock signal, and the decision block 285 asks whether this is the end of the time period. If the answer is negative, the signal flow loops back through the block 283, waiting for the next interrupt. If the answer is either of the decision blocks 282 or 285 is affirmative, the signal flow passes to a statement block 286, where the elapsed time is divided by the number of events to arrive at an average time per event, which is passed to a decision block 287 and also to a statement block 288. This latter block resets the timer 284 and the event counter in block 281. The decision block 287 asks whether the average time per event was less than X, between X and Y, or less than Y, with these three rates of events occurring on outputs 291, 292, and 293, respectively. These may go to the output unit 30 of FIG. 1, which, for example, can be a display unit as shown in FIG. 2 to activate the red, yellow, or green lamps 35, 36, and 37.

Figure 21:
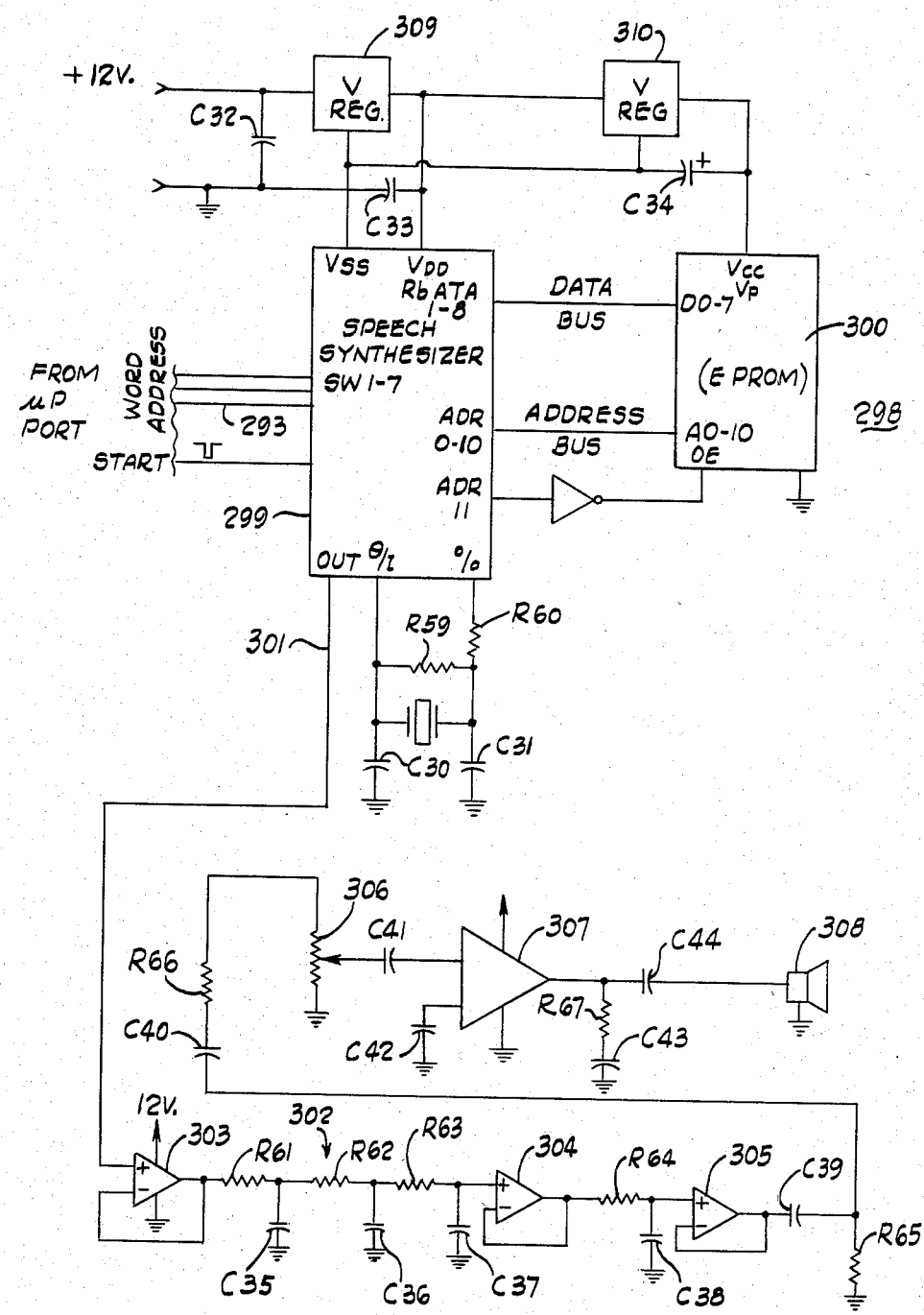
FIG. 21 is a schematic diagram of a speech synthesizer controlled by the output of the microprocessor.

Alternatively, the output lines 291, 292, and 293 may be passed to a voice synthesizer circuit 298 shown in FIG. 21. These three output lines 291, 292, and 293 are connected to switch inputs of a speech synthesizer module 299. An EPROM 300 would be previously encoded with a number of digitally encoded messages such as "Easy on the clutch, " "Please slow down for fuel efficiency, " "Less frequent use of the brake gives better fuel economy, " "Fewer steering movements provide a more comfortable ride, " "Riding the clutch or brake causes unnecessary wear, " etc. The speech synthesizer module 299 forms speech from this digitally encoded message putting the proper inflection, timing, frequency and pitch to the various combined syllables to make intelligible speech. This is passed on the output line 301 through a digital filter 302, which includes Op Amps 303, 304, and 305, with the signal then passed to a volume control 306, which is then amplified by a power amplifier 307. This supplies a loudspeaker 308. Voltage regulators 309 and 310 supply the regulated voltage to the module 299 and EPROM 300. By this circuit 298, the caution or unsatisfactory codes may be imparted to the subject, e.g., the driver of an automobile, by the synthetic voice rather than by some visual display which might distract the driver. The EPROM 300 can be digitally encoded with voice messages, which are interpreted by the left hemisphere of the brain of the driver. The EPROM 300 can also be encoded with a tuneful melody, either first or as background music to the voice messages, and this will have a positive reaction on the right brain hemisphere, for a balance of brain hemisphere input, and so that the voice message will be more acceptable to the driver. This entire circuit shown on FIG. 21 may be purchased from National Semiconductor, mounted on a printed circuit board.

In one practical circuit constructed in accordance with the invention generally as shown in FIGS. 1–17, the circuit components and values therefor were as follows:

| Resistance | Value | Resistance | Value |
| --- | --- | --- | --- |
| R1 | 100 Megohms | R37 | 330 Ohms |
| R2 | 1 Kilohm | R38, R39 | 12 Kilohms |
| R3, R4 | 2.2 Kilohm | R40, R41 | 10 Kilohms |
| R5, R6 | 1 Megohm | R42 | 120 Ohms |
| R7, R9 | 10 Kilohms | R45 | 220 Kilohms |
| R8 | 10 Kilohms | R46, R47 | 10 Kilohms |
| R10 | 2.2 Megohms | R48, R50 | 12 Kilohms |
| R11 | 1 Megohms | R49 | 10 Kilohms |
| R12 | 100 Kilohms | R51, R52 | 220 Kilohms |
| R13 | 1 Kilohms | R53, R54 | 10 Kilohms |
| R14 | 1 Megohm | R55, R58 | 220 Kilohms |
| R15, R17 | 10 Kilohms | R56, R57 | 100 Kilohms |
| R16, R18 | 10 Megohms | R59 | 1 Megohm |
| R19 | 1 Megohms | R60 | 1.5 Kilohm |
| R20 | 100 Kilohms | R61 | 9.1 Kilohms |
| R21 | 10 Megohms | R62 | 2.2 Kilohms |
| R22, R23 | 10 Kilohms | R63 | 22 Kilohms |
| R24 | 330 Kilohms | R64, R65 | 7.5 Kilohms |
| R25 | 5.6 Kilohms | R66 | 10 Kilohms |
| R26, R27 | 10 Kilohms | R67 | 10 Ohms |
| R28 | 6.8 Kilohms | 57 | 200 Kilohms |
| R29, R30 | 10 Kilohms | 58 | 1 Megohm |
| R31 | 100 Kilohms | 70 | 1 Megohm |
| R32 | 22 Kilohms | 78 | 6.8 Kilohms |
| R33 | 3.9 Kilohms | 81 | 5.6 Kilohms |
| R34, R35 | 47 Kilohms | 82 | 5.6 Kilohms |
| R36 | 6.8 Kilohms | 83 | 680 Ohms |
| | | 89 | 4.7 Megohm |
| | | 221 | 12 Kilohms |
| | | 224, 251 | 100 Kilohms |
| | | 228, 2 0 | 220 Kilohms |
| | | P1 | 10 Kilohms |
| | | 219 | 100 Kilohms |
| | | 235 | 10 Kilohms |
| | | 272 | 100 Kilohms |
| | | 306 | 50 Kilohms |

| Capacitor | Value | Component | Type |
| --- | --- | --- | --- |
| C1, C2 | 0.1 microfarad | op amp 52–55 | LM 324 |
| C3 | .01 microfarad | op amp 65–68 | LM 324 |
| C4 | .05 microfarad | op amp 72, 75, 76 | LM 339 |
| C5, C7 | .01 microfarad | F/V 24 | LM 331 |
| C6 | .02 microfarad | $\mu P$ 29 | INTEL 8748-8 |
| C8, C9 | .005 microfarad | Driver 85–87 | ULN 2801A |
| C10 | 180 picofarad | Display 45–47 | HP 5082 7433 |
| C11 | .02 microfarad | Q79, 79A | 2N 4401 |
| C12 | .05 microfarad | Q221 | 2N 4401 |
| C13 | 4700 picofarad | Gate 27 | 14070 |
| C14 | .05 microfarad | Gate 225, 275 | CD 4010 |
| C15, C17 | .01 microfarad | Gate 229, 236, 237 | CD 4009 |
| C16 | .02 microfarad | Gate 243, 244, 276 | CD 4009 |
| C18, C19 | .005 microfarad | Gate 226, 239 | 74 C 32 |
| C20 | 180 picofarad | Gate 246, 247, 248 | 74 C 32 |
| C21 | .02 microfarad | Gate 277 | 74 C 32 |
| C22 | .001 microfard | Op Amp 303, 304, 305 | LM 324 |
| C23 | 470 picofarad | Op Amp 307 | LM 386 |
| C24 | .01 microfarad | V Reg. 309 | LM 7808 |
| C25 | .01 microfarad | V Reg. 310 | LM 7805 |
| C26, C27 | 10 microfarad | | |
| C28, C29 | .5 microfarad | 299 | MM 54104 |
| C30 | 20 picofarad | EPROM 300 | MM 2716 |
| C31 | 50 picofarad | | |
| C32 | 22 mf. 25 volt | | |
| C33, 34 | 4.7 mf. 10 volt | | |
| C35, C38 | .1 microfarad | | |
| C36, C40 | .01 microfarad | | |
| C37 | 1000 picofarad | | |
| C39, 41, 42 | .1 microfarad | | |
| C43 | .05 microfarad | | |
| C44 | 250 microfarad 16 volt | | |
| 90 | .1 microfarad | | |
| 220, 223, 227 | .5 microfarad | | |
| 273 | .5 microfarad | | |

It will be seen from the general block diagram of FIG. 1 and the specific modifications of FIGS. 2, 7, 17, and 19, that there is disclosed a neuromotor response apparatus and method which measures neuromotor efficiency at two or more levels by comparing responses of two or more interacting individuals or two or more similar responses by one individual. In the case of vocal fluency of the modifications of FIGS. 2 and 7, the potential uses include organizational development to teach communication skills in staff training, hence evaluating interpersonal interaction. Evaluating handedness in terms of finger dexterity utilizing teletypewriter keys or the like is intrapersonal evaluation. Also, the evaluation of imbalance of neuromotor responses in the steering, acceleration and deceleration of a motor vehicle has utility for driver training in a vehicle or vehicle simulator in the apparatus of FIGS. 17 and 19. This may be used for retrospective evaluation of the driver's performance. It also has implications for developing the driver's contribution to fuel efficiency and limiting use of the brake. When a display panel such as that shown in FIG. 2 is used with the apparatus of FIG. 17, or 19, the pedal interruptions may be displayed on the left and the acceleration pedal actuations on the right. Also, the display may be a triple unit, with the clutch actuation display on the far left. With a quadruple unit display, the steering wheel movements may also be indicated.

A neuromotor response hiatus may be defined as the absence of all monitored neuromotor response for a predetermined time interval bounded by the predetermined neuromotor response. For the pedals alone, this may be defined as movement of the subject pedal without intervening movement of any other pedal. Including the steering wheel, the hiatus may be defined as movement of the subject vehicle control without intervening movement of any other monitored vehicle control. In this case, the apparatus has utility to serve as a "flight recorder" on a school bus and the like to identify driver error; to measure a driver's mental depression and coronary-prone behavior, e.g., suicide and susceptibility to heart attack. These conditions are manifested by frequent movements of the steering wheel. The apparatus also may be used to assess the driver's contribution to fuel efficiency, i.e., pumping the accelerator and wearing out the brakes prematurely by pumping the brake pedal excessively. Inefficient and potentially hazardous lane jumping would be manifested by frequent movements of the steering wheel. The failure to negotiate a curve properly could be manifested by both frequent and excessively long steering wheel movement. Preferably, the display should be presented only after the trip is completed upon turning off the ignition so as not to distract the driver enroute.

A high hiatus rate, e.g., in a person's voice, can be symptomatic of coronary-prone behavior, which can result in hormonal secretions that can be phasic or pulsatile, which in turn can influence blood glucose and the body's insulin requirement. Thus, in diabetics requiring frequent doses of extra insulin, the unsatisfactory or "red" code could trigger the actuation of an implanted insulin pump, and can provide an immediate beneficial biofeedback to the subject. A usual implantable insulin pump has an existing profile of insulin injection algorithmically built into its memory, which may be modified by different stress levels which are determined by the microprocessor 29. It can be used to modify the dispensing program of the pump.

In the embodiment of FIGS. 1-7, wherein the neuromotor response system is a voice-responsive system, then FIG. 8 shows some possible patterns of hesitation pauses. In the graph 199 of FIG. 8, there are many red code pauses. The green, yellow, and red code pauses may be characterized as satisfactory, caution, and unsatisfactory pause rates or frequency of pauses. The present apparatus introduces a microprocessor method of determining and displaying the frequency and duration of speech pauses considered to be useful in assessing brain hemisphere functions.

Pause or hiatus frequency is mediated by the left hemisphere, while pause duration is mediated by the right hemisphere. Impairment of Broca's Area on the left, such as by stroke, results in frequent pauses, while endogenous depression with psychomotor retardation is manifested by elongated pauses and originates from the right hemisphere.

Coordinated interaction between the left and right brain hemispheres is measured as the ability to decrease the rate of hesitation by varying the duration of pauses. Maximal adaptation is demonstrated by inverse correlation between frequency and duration. This is based on the equation, frequency times duration equals a constant, i.e., a finite amount of pause time is required to collect thoughts adequately.

Varying the cadence of vocal delivery from a few shorter pauses to less recurrent longer pauses imparts rhythm or emotional coloration to speech. The emotional component of speech is called prosody, a function of the right brain. Patients with right brain damage often demonstrate aprosodia, the ability to manage the propositional or left brain component of language but not the emotional component.

Thus, the present invention provides a measure of left brain function at three levels of fluency and of right brain function at three levels. It is hypothesized that a higher degree of prosody is present if there is a stepped increase compared with a stepped decrease in pause duration from low to middle to high fluency. For a person who has suffered depression, the pause pattern might be something like that shown in graph 199 in FIG. 8. Therefore, in order to increase prosody, it would be better for that patient to increase the duration of a pause, to gather his thoughts, and then to be able to speak for a period of time without any pauses. This could increase the number of yellow and green code pauses and decrease the number of red code pauses so that the subject could increase his fluency of speech. If equipment is being used by a cardiac patient, for example, and is being used in the monologue mode by actuating the switch 42 to the monologue position, then a disable switch 84 may be opened to disable the red indicator lamp 37. This disable switch 84 may be located on the rear of the panel, and may be actuated to the OFF position by the doctor, so that the cardiac patient will not know that he is always in the red code rate of pauses. The display driver circuit of FIG. 6 utilizes cross-point multiplexing, so particular segments of the seven-segment displays are connected in parallel, with the red indicator lamp 37 being the last one in the series before the final return connection to the cathodes. The disable switch 84 is then positioned in this series immediately preceding the red indicator lamp 37. This red indicator disabler switch allows the option to focus solely on prosody, which is appropriate for certain patients who would be unduly intimidated by a red light. Also, the monologue switch 42 will permit a cardiac patient or stroke victim to practice by himself in addition to being able to practice in a dialogue.

Viewing the dialogue as a single unit, cross-prosody is a new term defined as a stepped increase in duration from red to yellow to green utilizing at least one value from each speaker. This encourages collaboration in focused staff training, since both partners' scores are considered in attaining prosody, hence mitigating against a pace one partner might consider terse. Another indicator of interpersonal harmony is a closer approximation of partners' pause durations as efficiency levels increase.

From a review of at least 500 telephone calls using similar apparatus, it has been determined that the mean duration of hesitation pause was 1.5 seconds plus or minus one-third of a second. The individual may vary considerably from this mean or average and the apparatus may be used to establish a basic relationship between a teacher and his class. Students may be sorted into subgroups to match teachers with similarly paced behavior. A slow-paced teacher and fast-paced students will result in restless students; whereas, in the reverse case, the students will fail to get the point. In the monologue mode, a student may use the instrument for self-improvement. With the voice print circuit of FIG. 7, the teacher can monitor his presentation to the class. This may be done also in the monologue mode of FIG.

7, as shown in the last digital processor 210 in the group of digital processors.

The present apparatus and method identify pause durations at high, middle, and low coronary risk, and to match dominant pause durations in the dual display format to determine interpersonal harmony of pace at the 95 percent level of confidence given a normative sample mean of 1.5 seconds with a standard deviation of 0.33 seconds pause duration.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of the circuit and the combination and arrangement of circuit elements may be resorted to without departing from the spirit and the scope of the invention as hereinafter claimed.

What is claimed is:

1. A computing device for evaluation of human response, comprising in combination:
   input signal receiving means operable to receive first type signals from a signal generator of at least a first human subject;
   means to mesure the respective elapsed times between consecutive signals from said first human subject;
   means for sorting said elapsed times into at least two frequency levels;
   computing mens to determine the average elapsed time of each of said levels; and
   recording means operable to record on a time base the average frequency level and the average elapsed time of each level for at least said first human subject.

2. A computing device as set forth in claim 1, wherein said recording means includes indicating means to human sensors for transfer to the human brain the average frequency level and the average elapsed time of each level as determined by said computing means.

3. A computing device as set forth in claim 1, wherein said input signal receiving means includes voice print processing and identifying means.

4. A computing device as set forth in claim 1, including second input signal receiving means operable to receive second type signals from signal generators, and wherein said first-mentioned input signal receiving means is operable to receive said first type signals resulting from the response of the brain of the subject to said second type signals.

5. A human response system for determining the hiatus rate of a neuromotor response of a human subject, comprising in combination:
   transducer means responsive to at least one type of neuromotor response of the subject who is subjected to sensory inputs to the right and left hemispheres of the brain;
   hiatus means connected to said transducer means to determine each successive occurrence of a hiatus between predetermined neuromotor responses of the subject with each hiatus defined as the absence of all monitored neuromotor responses for a predetermined time interval bounded by the predetermined neuromotor responses;
   rate means connected to said hiatus means to determine the average hiatus rate in a given segment of the predetermined neuromotor response of the subject;
   sorting means to sort the average hiatus rate into one of at least two levels of response; and
   means to indicate the average time duration of the individual hiatuses for each of the at least two rate levels.

6. A human response system as set forth in claim 5, including means to indicate the average level of hiatus rate.

7. A human response system as set forth in claim 5, including voice means to indicate the average level of hiatus rate.

8. A human response system as set forth in claim 6, including means to juxtapose said dominant level indicator and said hiatus rate indicator.

9. A human response system as set forth in claim 5, wherein said indicating means includes a plurality of hiatus rate indicators with means to juxtapose said hiatus rate indicators in substantially vertical alignment with the indicator for the lowest hiatus rate positioned at the top.

10. A human response system as set forth in claim 5, including a disabler switch to disable the hiatus rate indicator of at least one level.

11. A human response system as set forth in claim 5, wherein said hiatus is in a response of a control of a motor vehicle or vehicle simulator.

12. A human response system as set forth in claim 5, wherein said hiatus is a movement of a pedal in a motor vehicle or vehicle simulator.

13. A human response system as set forth in claim 5, wherein said hiatus is a steering control response in a motor vehicle or vehicle simulator.

14. A human response system as set forth in claim 5, wherein said indicator means is a voice means.

15. A human response system as set forth in claim 5, wherein said indicator means is a combination of voice and music.

16. A human response system as set forth in claim 5, wherein said indicating means includes means indicating the hiatus time duration for each of two types of neuromotor responses.

17. A human response system as set forth in claim 16, wherein said two types of neuromotor responses are from the same human subject.

18. A human response system as set forth in claim 5, wherein said indicating means includes means indicating the average hiatus time duration for each of two persons intercommunicating.

19. A human response system as set forth in claim 18, including means to indicate the percent of communicating time relative to the total time for at least one of the persons.

20. A human response system as set forth in claim 18, wherein one of the two persons is a local person and the other is remotely situated, and wherein said indicating means includes means for indicating on a display panel the response of the local person and the other person with the response of the local person to the left of the response of the other person.

21. A human response system as set forth in claim 18, including a disabler switch to disable the indicator means of one of the two persons.

22. A human response system as set forth in claim 18, including an input signal level indicator for each of the two persons.

23. A human response system as set forth in claim 18, including an input signal level indicator for each of the two persons, and wherein said indicating means includes an average hiatus rate indicator for each of the two persons.

24. A human response system as set forth in claim 23, including a display panel, wherein said input signal level indicators are green lamps positioned near the bottom of said display panel, said hiatus rate indicators are a plurality of indicators for each person and are disposed with the lowest hiatus rate indicator on the top and are green lamps, and said hiatus rate indicators for the highest hiatus rate are red lamps framed by said green lamps.

25. A human response system as set forth in claim 18, wherein said neuromotor intercommunication is by voices, wherein said transducer means is responsive to said voices to develop analog voice signals, and including means to convert said analog voice signals to digital signals to supply to a computer said digital signals corresponding to said analog voice signals.

26. A human response system as set forth in claim 25, wherein said converting means includes a bandpass circuit to transform analog voice signals to digital signals in a digital output circuit.

27. A human response system as set forth in claim 18, wherein said neuromotor intercommunication is by voices, including bandpass means connected to the output of said transducer means and having a saturated comparator and frequency-to-analog conversion means.

28. A human response system as set forth in claim 27 wherein said bandpass means includes a window comparator to effect a sharp-skirted bandpass means.

29. Apparatus for determining human response patterns of a human subject, comprising in combination:
transducer means responsive to at least one human response of the subject;
hiatus means connected to the transducer means for determining each of successive hiatuses between human responses of the subject defined as the absence of all monitored human responses for a predetermined time interval bounded by responses of the predetermined human response;
rate means connected to said hiatus means for determining the rates of the successive hiatuses;
means to sort the hiatus rates into at least one of two levels; and
output means connected to the sorting means and having an output to represent at least one level of hiatus rates, characterized in that the output means is responsive to both the average hiatus rate and the average time duration of the hiatuses of such level.

30. Apparatus as set forth in claim 29, wherein said transducer means is responsive to the speech of the subject.

31. Apparatus as set forth in claim 29, wherein said transducer means is responsive to the movement of controls in a motor vehicle or vehicle simulator.

32. Apparatus as set forth in claim 29, wherein said transducer means is responsive to the neuromotor output of another person with whom the subject is communicating and said hiatus means is connected to the transducer means to determine hiatuses of a duration longer than in the order of one second defined by joint noncommunication of both persons bounded by the neuromotor output of the subject.

33. Apparatus as set forth in claim 32, wherein said output means indicates the average hiatus rate and the average of the time duration of the hiatuses of the respective level for each of the two persons.

34. An information feedback voice monitoring system, comprising in combination:
transducer means connected to be responsive to the voice of a subject and to the voice of another in a dialogue setting;
a control circuit connected to said transducer means;
means in said control circuit to determine the occurrence of each of successive hesitation pauses in the speech of the subject, each of which hesitation pauses is defined as a joint silence of one second or more bounded by the speech of such subject during a dialogue;
means in said control circuit to determine the frequency of hesitation pauses in the speech of the subject during a dialogue with said another person;
a sensory output having signal codes of satisfactory, caution and unsatisfactory associated with a numerical indication of the time duration of the pause; and
a microprocessor connected to the output of said pause and frequency determining means and having an output to said sensory output to emphasize only one signal code of satisfactory, caution or unsatisfactory, depending on the number of pauses per minute being 0 to about 1.5, about 1.5 to 2, and more than 2, respectively, and to indicate the average time duration of those hesitation pauses which fall within the pause per minute range of 0 to about 1.5, about 1.5 to 2, and more than 2, respectively.

35. A voice monitoring system for determining the voice fluency of a human subject, comprising in combination;
transducer means responsive to the voice of the subject and to the voice of another with whom the subject may have a dialogue or solely responsive to the voice of the subject engaged in a monologue;
pause means connected to said transducer means to determine the occurrence of each of successive hesitation pauses in the voice of the subject with each hesitation pause defined as a pause of a time duration longer than in the order of one second of joint silence of both voices bounded by the voice of the subject;
rate means connected to said pause means to determine the average rate of hesitation pauses in a given voice segment of the subject;
sorting means to sort the hesitation pauses into at least two levels of fluency; and
means to indicate the average time duration of the individual hesitation pauses for each of the two levels.

36. The method of determining hiatus frequency and duration of a human neuromotor response, comprising in combination:
determining the occurrence of each of a plurality of hiatuses in the neuromotor response of a subject, each hiatus defined as a lapse in the continuity of the response;
measuring the average hiatus rate in a given time segment of a response;
sorting the hiatuses into at least two rate levels; and
indicating to human sensors the hiatus rate level which was dominant relative to the others of the at least two rate levels and the average hiatus time duration of such level.

37. The method as set forth in claim 36, wherein said neuromotor response is the voice of the subject.

38. The method as set forth in claim 36, wherein said neuromotor response is the movement of a control in a motor vehicle or a vehicle simulator.

39. The method as set forth in claim 36, including determining two neuromotor responses of the same subject; and indicating the average hiatus duration for each of the two neuromotor responses.

40. The method as set forth in claim 36, including determining a neuromotor response for each of two persons communicating with each other.

41. The method as set forth in claim 36, including juxtaposing the dominant rate level indicator and the average hiatus duration indicators.

42. The method of determining a human subject's pause frequency and pause duration while having a dialogue, comprising in combination:
measuring the length of each of one or more pauses in the speech of the subject bounded by speech of the subject and establishing each of such pauses as a hesitation pause when the length thereof exceeds about one second of time;
determining the rate of hesitation pauses in the speech of said subject while having a dialogue;
assigning a satisfactory code to those hesitation pauses in the speech of said subject which occur after more than about one minute of speech without a hesitation pause;
assigning a caution code to the second hesitation pause which occurs during any one minute of the dialogue;
activating a caution indicator indicating an average of about one to two hesitation pauses per minute; and
determining and displaying the average time duration of the dominant one of the satisfactory and caution code pauses for said subject.

43. The method as set forth in claim 42, including:
assigning an unsatisfactory code to the third and any succeeding hesitation pause occurring during any one minute of the dialogue; and
activating an unsatisfactory indicator upon the occurrence of an average of more than about two hesitation pauses per minute.

44. The method as set forth in claim 42, including determining and displaying the average time duration of said unsatisfactory code pauses.

45. The method as set forth in claim 42, including indicating the percent of speech time of the subject relative to the total time of the dialogue.

46. The method as set forth in claim 42, including indicating the percent of speech time of each of the subject and the other person relative to the total time of the dialogue.

47. The method as set forth in claim 42, including determining the rate of hesitation pauses and duration of each such pause of another person with whom the subject may have a dialogue.

48. The method as set forth in claim 47, including determining and displaying the average time duration of each of said satisfactaory and caution code pauses for said another person.

49. The method as set forth in claim 48, including activating an unsatisfactory indicator upon the occurrence of an average of more than two hesitation pauses per minute in the speech of said another person.

* * * * *

UNITED STATES PATENT AND TRADEMARK OFFICE
CERTIFICATE OF CORRECTION

PATENT NO. : 4,543,957

DATED : October 1, 1985

INVENTOR(S) : Ernest H. Friedman, Gary G. Sanders, Steven L. Hunter

It is certified that error appears in the above-identified patent and that said Letters Patent are hereby corrected as shown below:

Col. 8, line 58, "10" should be --20--

Col. 23, line 65, under column marked Resistance, "224,251" should be --224,231--.

Col. 23, line 66, under column marked Resistance, "228,2 0" should be --228,230--.

Col. 27, claim 1, line 31, "mens" should be --means--.

Signed and Sealed this

First Day of July 1986

[SEAL]

Attest:

DONALD J. QUIGG

Attesting Officer

Commissioner of Patents and Trademarks